United States Patent
Motoki et al.

(10) Patent No.: US 7,179,223 B2
(45) Date of Patent: Feb. 20, 2007

(54) ENDOSCOPE APPARATUS HAVING AN INTERNAL CHANNEL

(75) Inventors: Nobuyuki Motoki, Hachioji (JP); Kiyoshi Miyake, Asaka (JP)

(73) Assignee: Olympus Optical Co., Ltd. (JP)

(*) Notice: Subject to any disclaimer, the term of this patent is extended or adjusted under 35 U.S.C. 154(b) by 81 days.

(21) Appl. No.: 10/633,668

(22) Filed: Aug. 5, 2003

(65) Prior Publication Data

US 2004/0133075 A1 Jul. 8, 2004

(30) Foreign Application Priority Data

Aug. 6, 2002 (JP) ............... 2002-228936
Feb. 5, 2003 (JP) ............... 2003-028831

(51) Int. Cl.
*A61B 1/00* (2006.01)
*A61B 1/018* (2006.01)

(52) U.S. Cl. ............ 600/131; 600/102; 600/104; 600/146

(58) Field of Classification Search ........ 600/102, 600/104, 131, 146, 147, 152, 136; 604/95.01, 604/95.03
See application file for complete search history.

(56) References Cited

U.S. PATENT DOCUMENTS 4,489,728 A * 12/1984 Matsuo et al. ............ 600/146
4,696,544 A * 9/1987 Costella ................. 385/118
4,848,817 A   7/1989 Hasegawa
4,919,112 A * 4/1990 Siegmund ............... 600/136
5,373,317 A   12/1994 Salvati et al.
5,431,150 A * 7/1995 Yabe et al. .............. 600/121
5,447,148 A * 9/1995 Oneda et al. ............ 600/131
6,352,503 B1 * 3/2002 Matsui et al. ............ 600/104
6,554,766 B2 * 4/2003 Maeda et al. ............ 600/132
6,569,084 B1 * 5/2003 Mizuno et al. ........... 600/102
2004/0015050 A1 * 1/2004 Goto et al. ............... 600/104
2005/0119527 A1 * 6/2005 Banik et al. ............. 600/117

* cited by examiner

*Primary Examiner*—John P. Leubecker
(74) *Attorney, Agent, or Firm*—Dickstein, Shapiro, LLP.

(57) ABSTRACT

An endoscope apparatus having an internal channel comprises a scope portion in which a flexibly bending portion is provided at an elongated insert portion having a flexibility, the insert portion being inserted into a space which is a target of inspection, and a manipulating device inserting channel is formed, the channel being capable of loading therein a predetermined manipulating device which advances the inside of the insert portion to its distal end side, a remote controller which operates the flexibly bending portion by a joystick, and a connecting device which connects the scope portion and the remote controller to be integrally linked with each other at a position where an operation of the joystick and an operation for inserting the manipulating device through a proximal opening end do not interfere with each other.

23 Claims, 30 Drawing Sheets

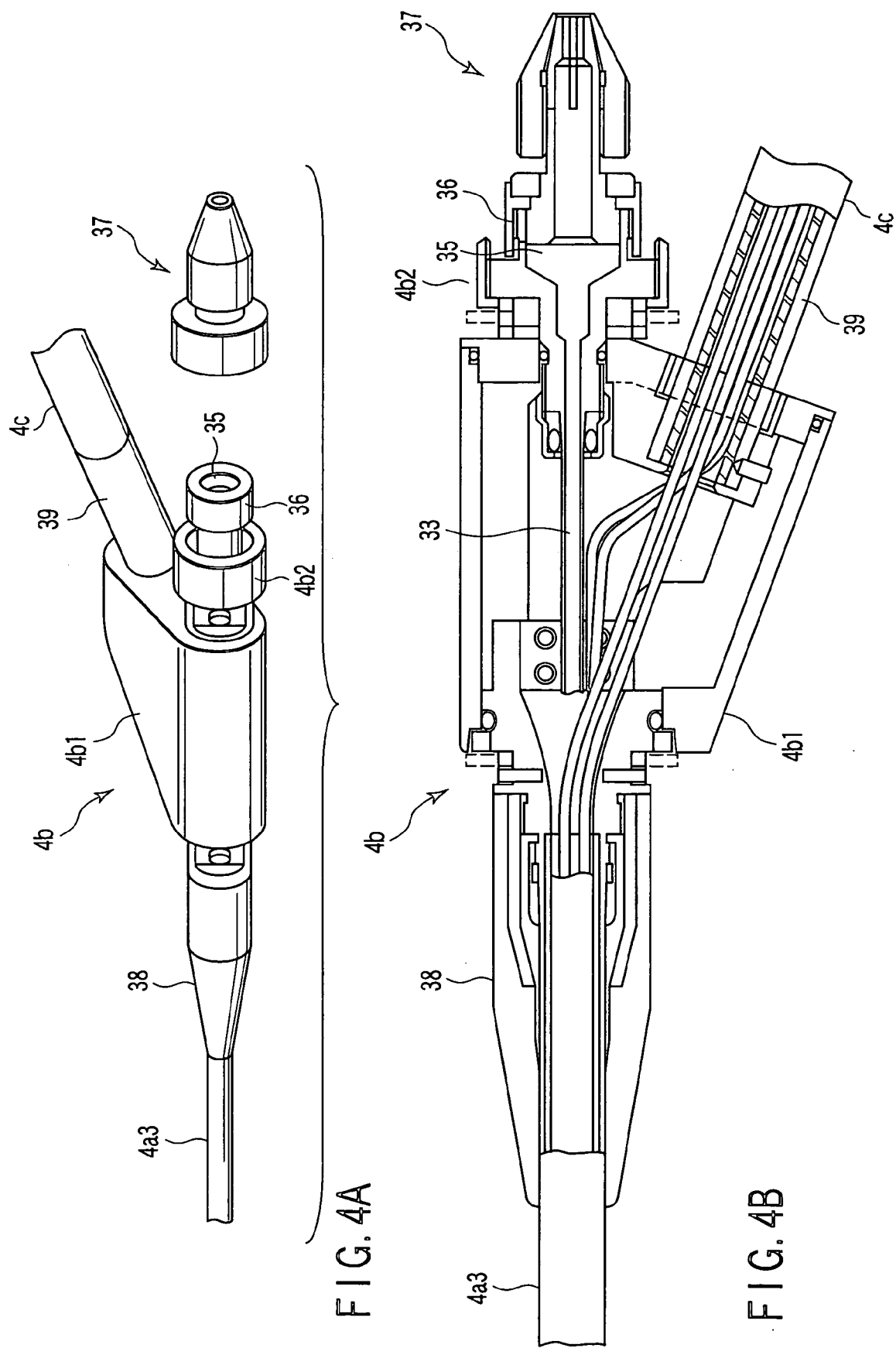

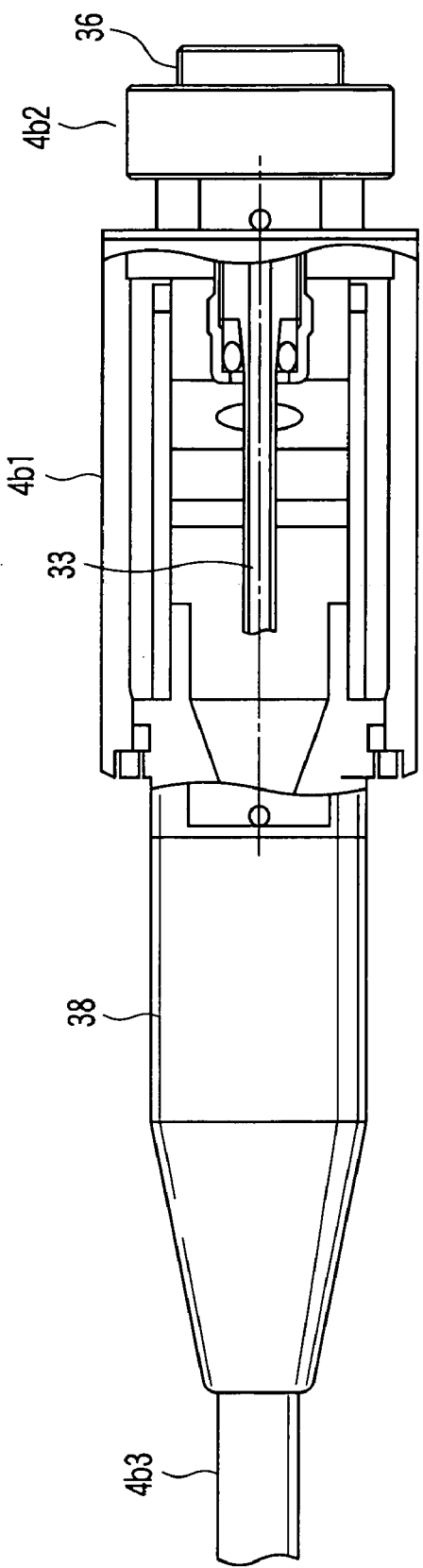
F I G. 5A
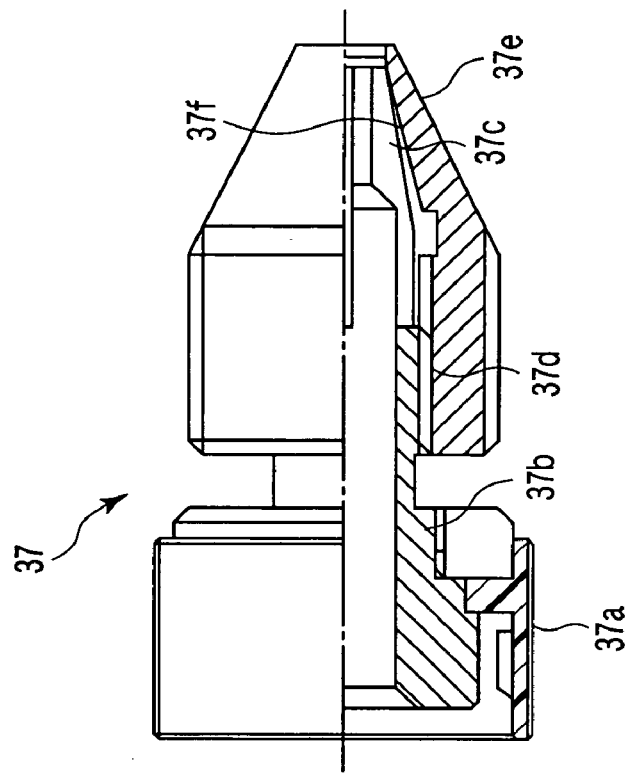
F I G. 5B

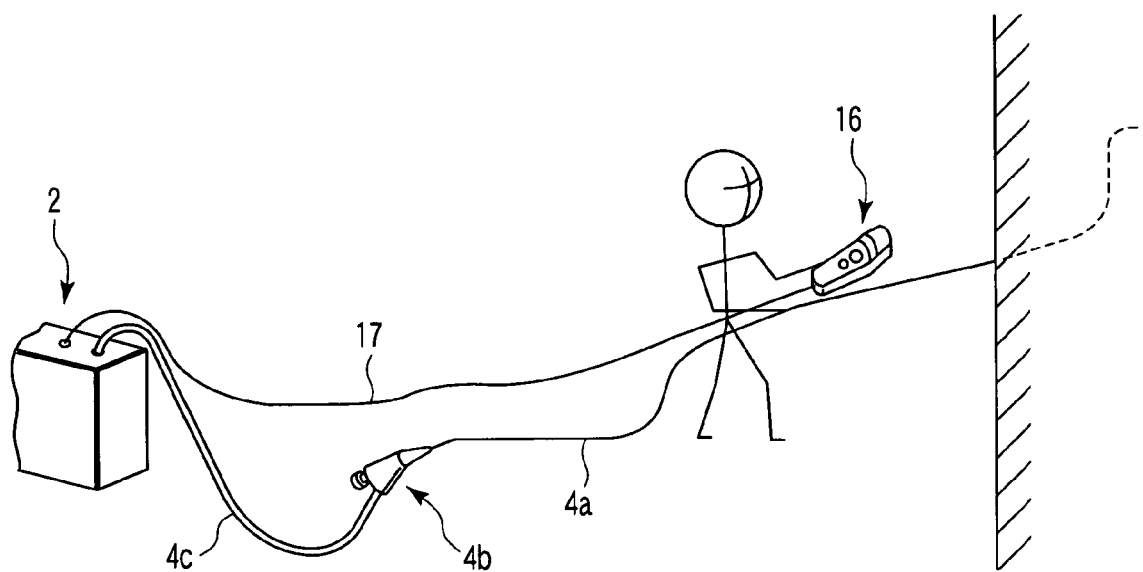
F I G. 11
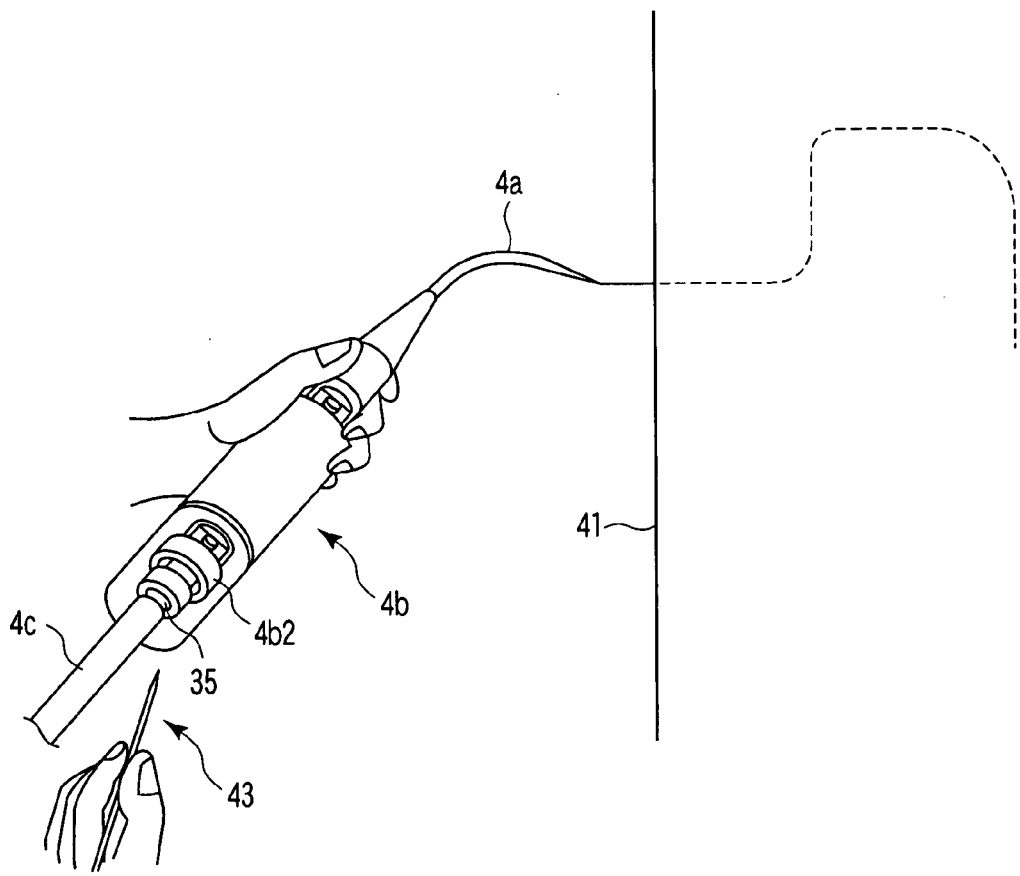
F I G. 12

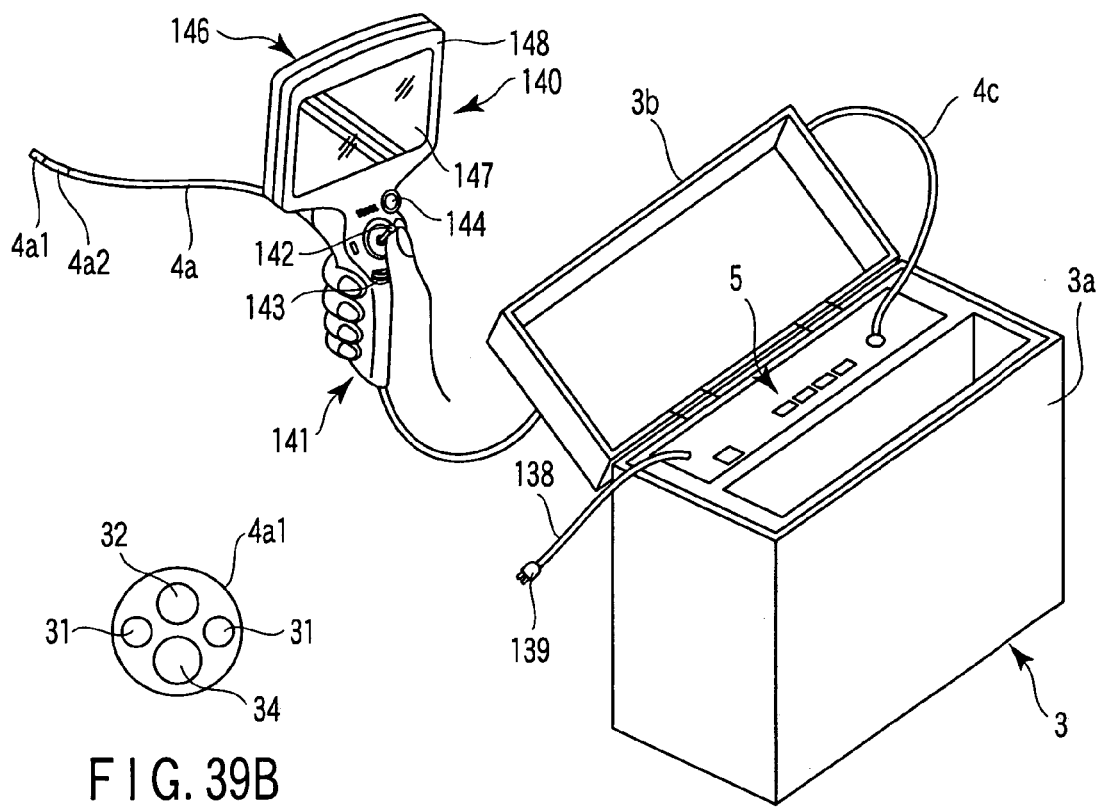
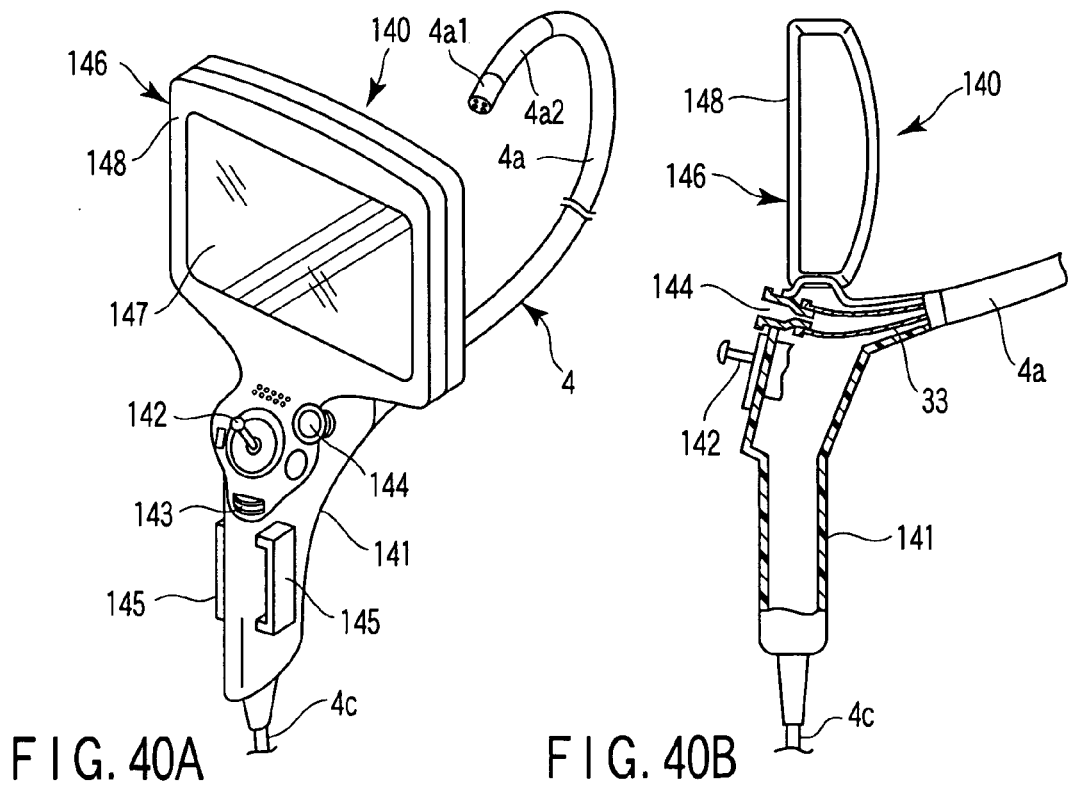

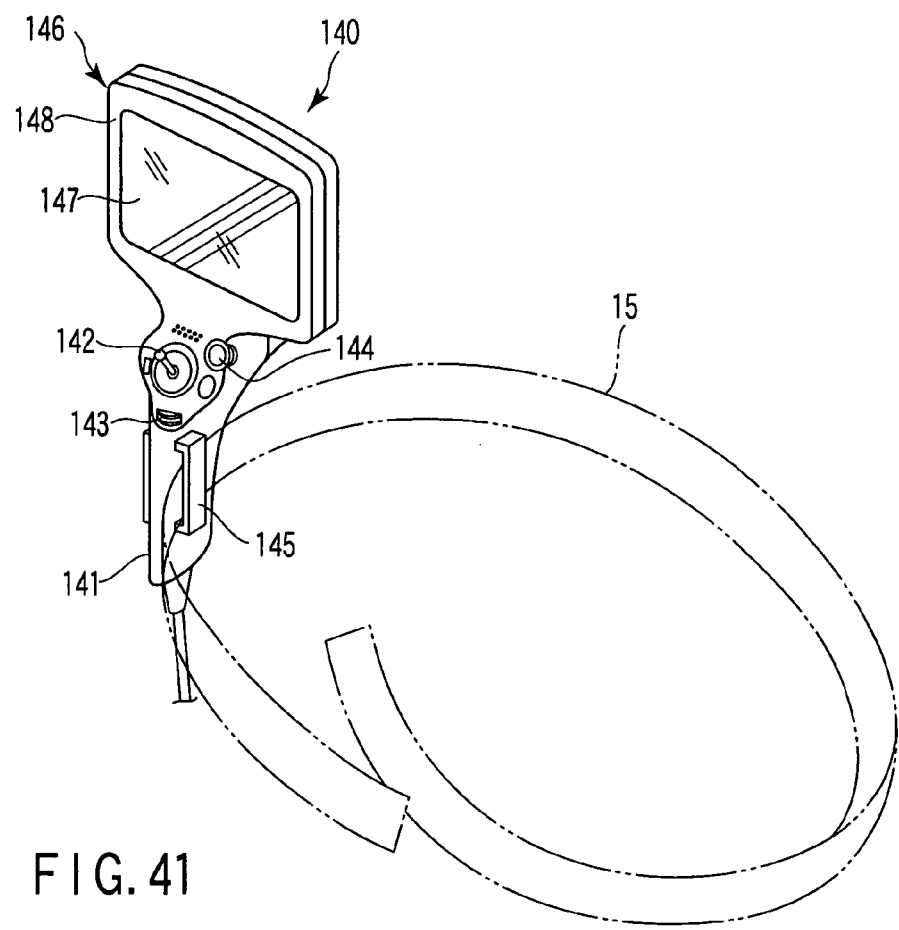
FIG. 41
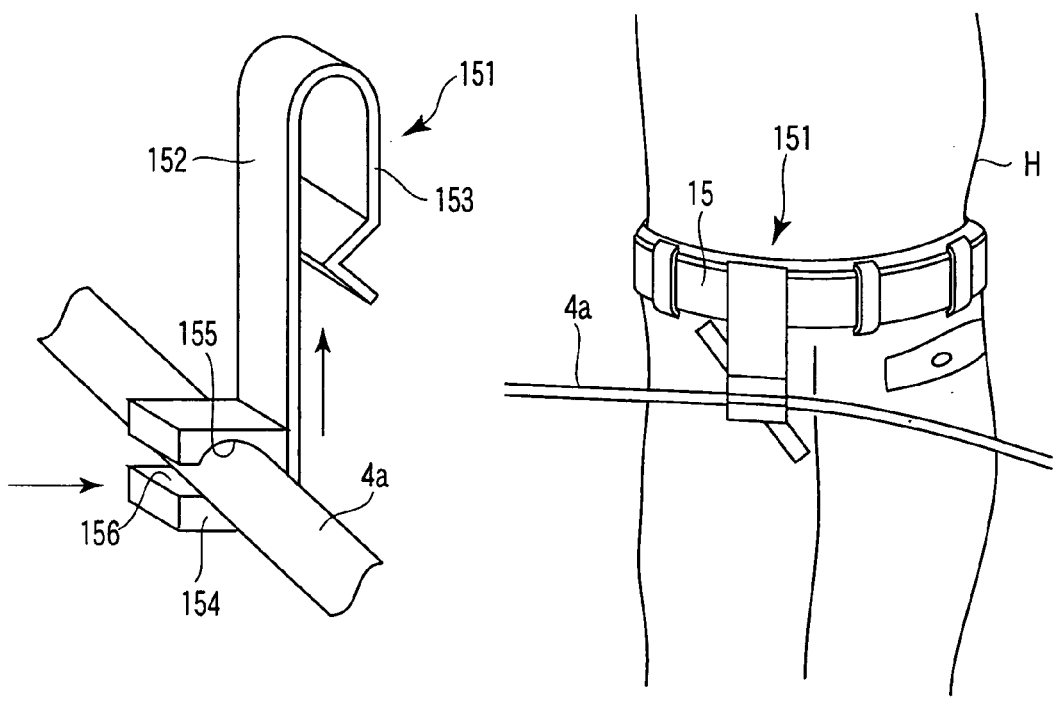
FIG. 43
FIG. 44

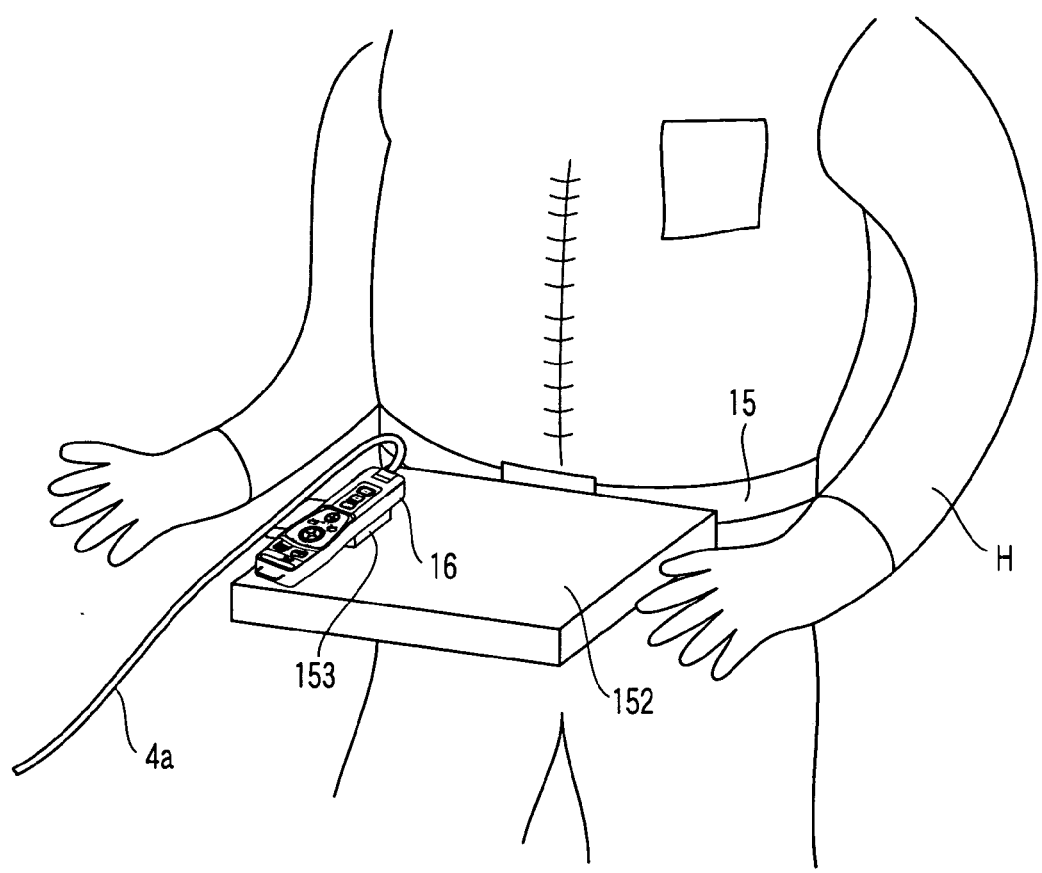
F I G. 45
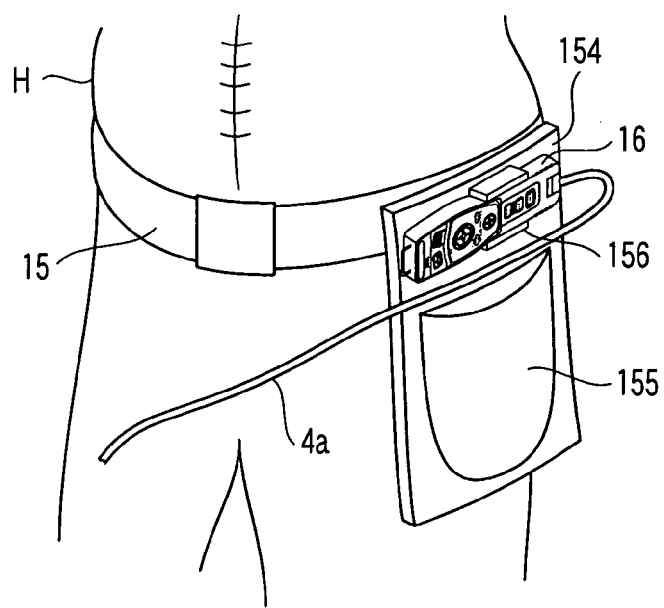
F I G. 46

ENDOSCOPE APPARATUS HAVING AN INTERNAL CHANNEL

CROSS-REFERENCE TO RELATED APPLICATIONS

This application is based upon and claims the benefit of priority from the prior Japanese Patent Application No. 2002-228936, filed Aug. 6, 2002; and No. 2003-028831, filed Feb. 5, 2003, the entire contents of which are incorporated herein by reference.

BACKGROUND OF THE INVENTION

The present invention relates to an endoscope apparatus mainly used in the industrial field, the endoscope apparatus being inserted into a space which is a target of inspection such as an inside of a pipe, the endoscope apparatus observing a site inside the space or an internal state thereof.

In general, in an endoscope apparatus for industrial use, a frontal operating portion 160 is linked with a proximal end part of an elongated insert portion 161 to be inserted into a space which is a target of inspection such as the inside of a pipe, as shown in FIG. 47. As such an example, there is shown an exemplary configuration in which a head portion (not shown) is provided at the most distal end part side of the insert portion, the head portion having incorporated therein an observation optical system for observation, an illustration optical system and the like. Further, a flexibly bending portion which can be bent in an arbitrary vertical or horizontal direction is provided at the rear of the head portion. A plurality of, for example, four flexibly bending operation wires are extended to a frontal side (to a proximal end part) from a distal end of the flexibly bending portion. These flexibly bending operation wires are linked with a flexibly bending operation mechanism (not shown) provided at the frontal operating portion 160.

An operating knob 163 for driving the flexibly bending operation mechanism and operating the flexibly bending portion to be bent is provided at this operating portion 160. By operation of this operating knob 163, the flexibly bending operation mechanism is driven, each flexibly bending operation wire is pulled, and the flexibly bending portion is operated to be flexibly bent.

An internal channel (manipulating device inserting channel) for inserting a manipulating device such as forceps therein is provided at the insert portion of the endoscope. A distal operating end of the internal channel is formed at the head portion of the insert portion 161.

A forceps opening (proximal opening end) 162 of this internal channel is provided at the operating portion 161. An operating portion main body 164 having the operating knob 163 or the like provided thereat, and a grip portion 165 that is gripped by a user are provided at the operating portion 160. Then, it is often that the forceps opening 162 of the internal channel is disposed at the grip portion 165 of the operating portion 160 as shown in FIG. 47, or the forceps opening is disposed at a terminal portion of the operating portion main body 164 of an operating portion 166 as shown in FIG. 48.

In recent years, with advancement of electrically driving of a flexibly bending mechanism, as its flexible bending input means, the manual operating knob 163 may be replaced with electrically driven flexibly bending input means such as a joystick 167 disclosed in U.S. Pat. No. 5,373,317, for example. This joystick 167 generates a signal corresponding to a tilt angle of the flexibly bending portion.

However, at the operating portion main body disclosed in U.S. Pat. No. 5,373,317, a motor or monitor for electrically driven bending is disposed, and thus, the operating portion main body is heavy in weight and is large in size, which means that an operator is easily tired. It is not necessary that operating input means is always provided at the operating portion 160 (166) at the rear end side of the insert portion 161.

Because of this, flexibly bending input means such as a joystick 167 is considered to be provided independently in a place other than the operating portion 160 (166) at the rear end side of the insert portion 161. In this case, when an attempt is made to carry out only a flexibly bending operation when the endoscope apparatus is used, the joystick 167 is operated in a place other than the operating portion 160 (166), whereby the insert portion 161. may be gripped at an arbitrary position. In addition, when an attempt is made to carry out only a forceps operation, the forceps may be operated at the forceps opening 162 or in the vicinity thereof in a state in which the grip portion 165 of the operating portion 160 ((166) is gripped.

However, as in a conventionally configured apparatus, when the joystick 167 and operating portion 160 (166) are present in different places from each other, an operation of the joystick 167 and a forceps operation from the forceps opening 162 are carried out individually in different places from each other. Thus, an operation of the conventional endoscope apparatus shown in FIGS. 47 and 48 cannot be carried out. Therefore, the joystick 167 and forceps opening 162 must be disposed such that their respective operations do not interfere with each other in such a range that an operator's hand reaches.

In addition, in the conventionally configured endoscope apparatus, an operator always grips an operating portion during inspection of the endoscope apparatus. Since the operator always supports the mass of this operating portion, he/she feels fatigue as a work time increases. For example, in an endoscope apparatus for industrial use, an elongated insert portion is used in order to inspect a deep part of plant, for example, via an endoscope. The operator supports the mass of the apparatus, and thus, the operator's burden increases more significantly.

In endoscope inspection, an advancing/retracting operation or a twisting operation of the insert portion is an important work. In these works, the operator always grips the operating portion by one hand, and operates the insert portion by the other hand. In this situation, since both hands of the operator cannot be used, the operator cannot carry out other operations, for example, an operation for inserting a manipulating device into a forceps opening of the operating portion. As a result, operation by two or more operators is carried out, and is poor in usability.

BRIEF SUMMARY OF THE INVENTION

It is an object of the present invention to provide an endoscope apparatus with good operability, the endoscope apparatus being capable of easily carrying out both of a flexibly bending operation of a flexibly bending portion due to an operation of a flexibly bending input portion and an operation of a manipulating device or the like.

According to the present invention, in order to solve the above described problem, there is provided an endoscope apparatus comprising: an input device which comprises: an elongated insert portion having flexibility, the insert portion being inserted into a space which is a target of inspection; and a flexibly bending operation portion to operate a flexibly bending portion provided at the insert portion to be flexibly bent; a manipulating device inserting channel which communicates between a distal opening end that opens at a distal end side of the insert portion and a proximal opening end that opens at a proximal end of the insert portion; and a linking portion which detachably linking between a peripheral portion at the proximal opening end in the manipulating device inserting channel and the input device, wherein the linking portion disposes the proximal opening end of the manipulating device inserting channel at a position which does not interfere with an operating region of the flexibly bending operation portion in the input device in a state in which a link is established between the input device and the peripheral portion of the proximal opening end.

In addition, there is provided an endoscope apparatus comprising: an insert portion which inserts a flexibly bending portion having flexibility, the flexibly bending portion being provided at a distal end side, into a space which is a target of inspection; a manipulating device inserting channel which loads therein a predetermined manipulating device advancing from a proximal end side of the insert portion to a distal end side of the insert portion; a flexible bending operation portion to flexibly bend the flexibly bending portion of the insert portion remotely by a rod portion operation; and a connecting device which mounts the flexibly bending operation portion to make the flexibly bending operation portion and the insert portion adjacent to each other, and integrally links the operation portion and the insert portion with each other such that an operating space of the rod portion operation and a loading space required for loading the predetermined manipulating device therein do not overlap each other.

Further, there is provided an endoscope apparatus comprising: an elongated insert portion to be inserted into an object; an operating portion which operates the insert portion; and a connecting portion which detachably connects both or any one of the insert portion and the operating portion to a portion to be mounted that is provided at any one of a mount tool at an operator's body side or a peripheral device.

Moreover, there is provided an endoscope apparatus comprising: an insert portion which inserts a flexibly bending portion having flexibility, the flexibly bending portion being provided at distal end side, into a space which is a target of inspection; a manipulating device inserting channel which loads therein a predetermined manipulating device advancing from an opening end at the proximal end side of the insert portion to an opening end at the distal end side of the insert portion; a flexibly bending operation portion having a rod portion to flexibly bend the flexibly bending portion of the insert portion remotely and a proximal opening end provided out of an operating range of the rod portion; and a display portion provided upward of the flexibly bending operation portion, the display portion displaying a state of the flexibly bending portion by an operation of the rod portion.

The endoscope apparatus configured as described above carries out an input operation by the input device and a manipulating device operation from the manipulating device inserting channel when a link between the input device and the manipulating device inserting channel is released. The proximal end opening end of the manipulating device inserting channel is disposed at a position which does not interfere with an operating region of the flexibly bending operation portion in the input device during a link between the input device and the manipulating device inserting channel. As a result, the input operation by the input device and the manipulating device operation from the manipulating device inserting channel can be carried out without any interference with each other.

In addition, both or any one of the insert portion and the operating portion are removably mounted on a connecting portion with respect to a portion to be mounted, that is provided at any one of a mount tool at an operator's body side or a peripheral device.

BRIEF DESCRIPTION OF THE SEVERAL VIEWS OF THE DRAWING

FIG. 4A is a perspective view showing a state in which a fixing bracket of a hook type manipulating device is removed from a forceps opening of the grip portion in the endoscope apparatus according to the first embodiment;

FIG. 4B is a longitudinal cross section showing an internal configuration of the grip portion in the endoscope apparatus for industrial use;

FIG. 5A is a side view showing a partial cross section of the forceps opening of the grip portion in the endoscope apparatus for industrial use according to the first embodiment;

FIG. 5B is a side view showing a partial cross section of the fixing bracket of the hook type manipulating device;

FIG. 11 is an illustrative view for illustrating a work of inserting the insert portion in a state in which the remote controller and the grip portion of the scope portion are separated from each other in the endoscope apparatus for industrial use according to the first embodiment;

FIG. 12 is a perspective view showing a state in which the forceps is inserted into the forceps opening of the grip portion when the endoscope apparatus for industrial use according to the first embodiment is used;

FIG. 39A is a perspective view showing a schematic configuration of an entire endoscope apparatus for industrial use according to a twelfth embodiment of the present invention;

FIG. 39B is a plan view showing a distal end face of a head portion in the endoscope apparatus for industrial use;

FIG. 40A is a perspective view showing an operating portion in the endoscope apparatus for industrial use according to the twelfth embodiment;

FIG. 40B is a side view showing a partial cross section of the operating portion;

FIG. 41 is a perspective view showing a state in which the operating portion of the endoscope apparatus according to the twelfth embodiment is inserted into a belt;

FIG. 43 is a perspective view showing a clip portion of the endoscope apparatus for industrial use according to the thirteenth embodiment;

FIG. 44 is a schematic view showing a state in which an insert portion is held at the clip portion of the endoscope apparatus for industrial use according to the thirteenth embodiment;

FIG. 45 is a perspective view of essential portions showing a fourteenth embodiment of the present invention;

FIG. 46 is a perspective view of essential portions showing a fifteenth embodiment of the present invention;

DETAILED DESCRIPTION OF THE INVENTION

Hereinafter, preferred embodiments of the present invention will be described in detail with reference to the accompanying drawings.

Figure 1:
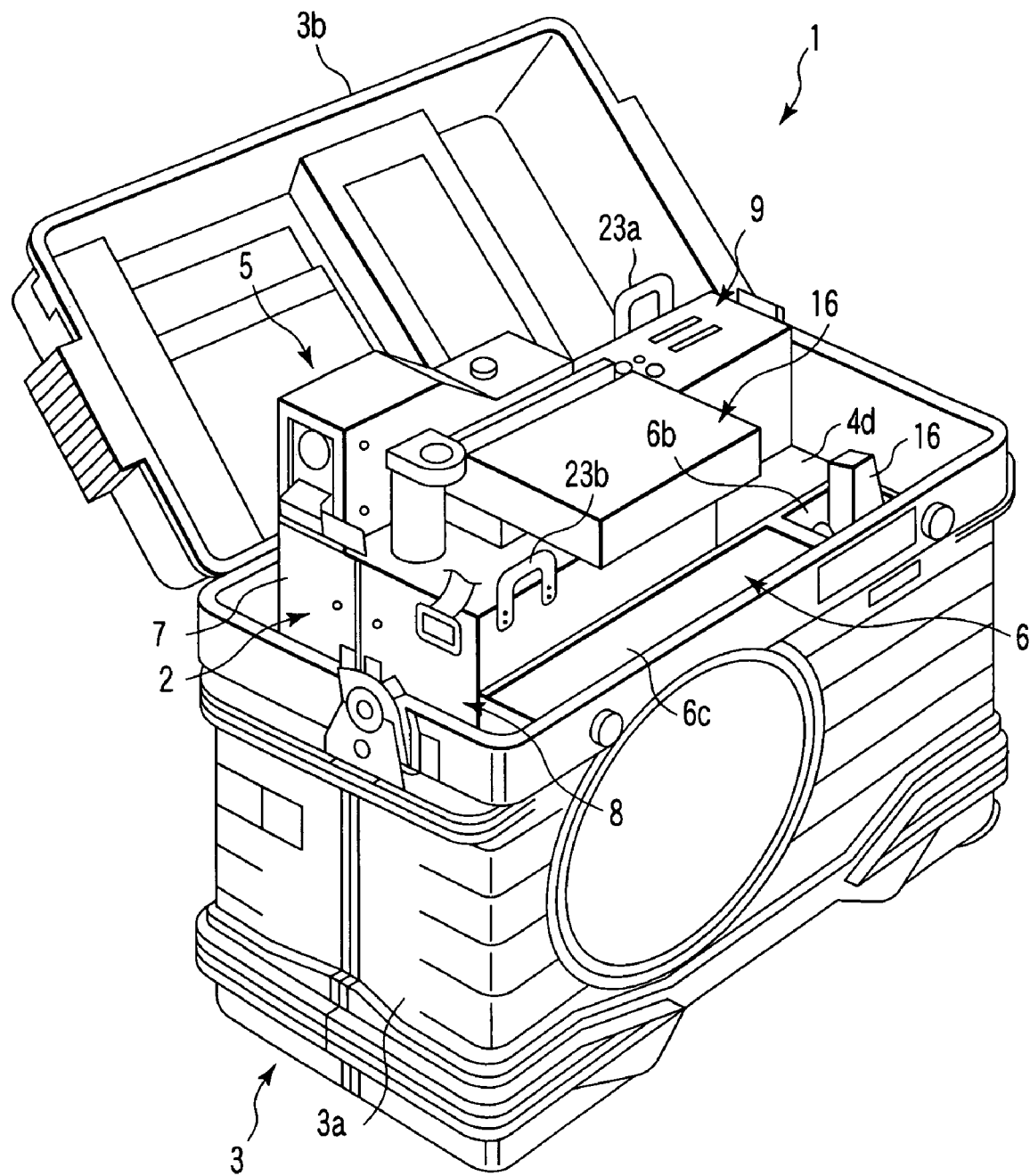
FIG. 1 is a perspective view of an entire endoscope apparatus for industrial use showing a state in which a lid of an endoscope housing case is opened in the endoscope apparatus for industrial use according to a first embodiment of the present invention.

First, a first embodiment of the present invention will be described with reference to FIGS. 1 to 14. FIG. 1 shows an endoscope apparatus 1 for industrial use according to the present invention.

Figure 2A:
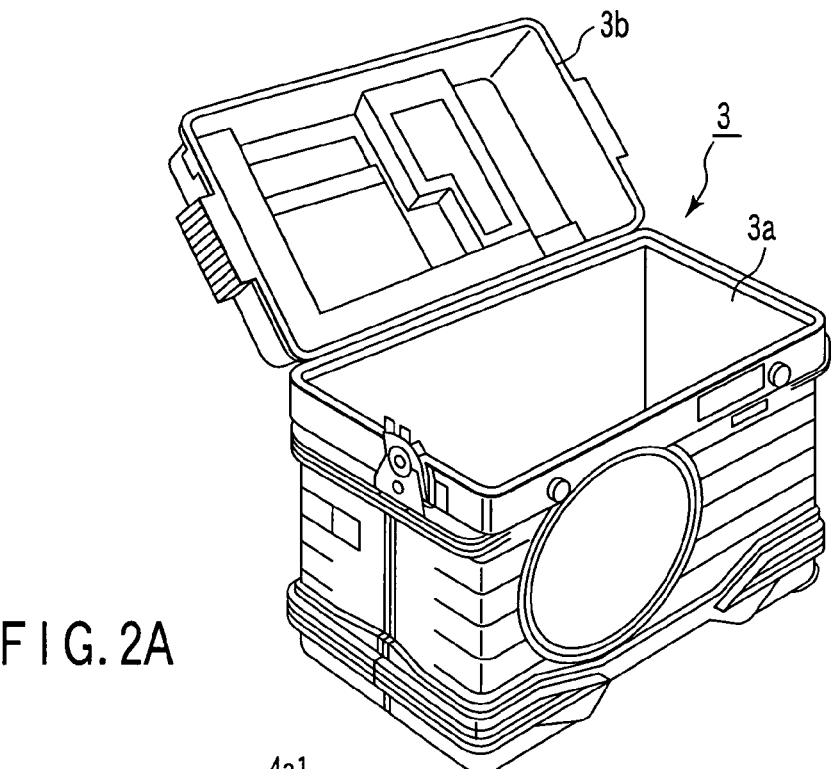
FIG. 2A is a perspective view showing the endoscope housing case in the endoscope apparatus for industrial use according to the first embodiment.

This endoscope apparatus 1 is roughly composed of: an assembling unit having constituent elements of an endoscope integrally assembled therein; and an endoscope housing case 3 for removably housing the assembling unit 2. As shown in FIG. 2A, the endoscope housing case 3 is composed of: a box-shaped case main body 3a whose top face is opened; and a lid 3b for opening and closing the top face opening. This lid 3b is turnably linked with one side part of the top face opening of the case main body 3a via a hinge portion (not shown). FIG. 1 shows a state in which the assembling unit 2 is housed in the endoscope housing case 3, and the lid 3b of the case main body 3a is opened.

Figure 2B:
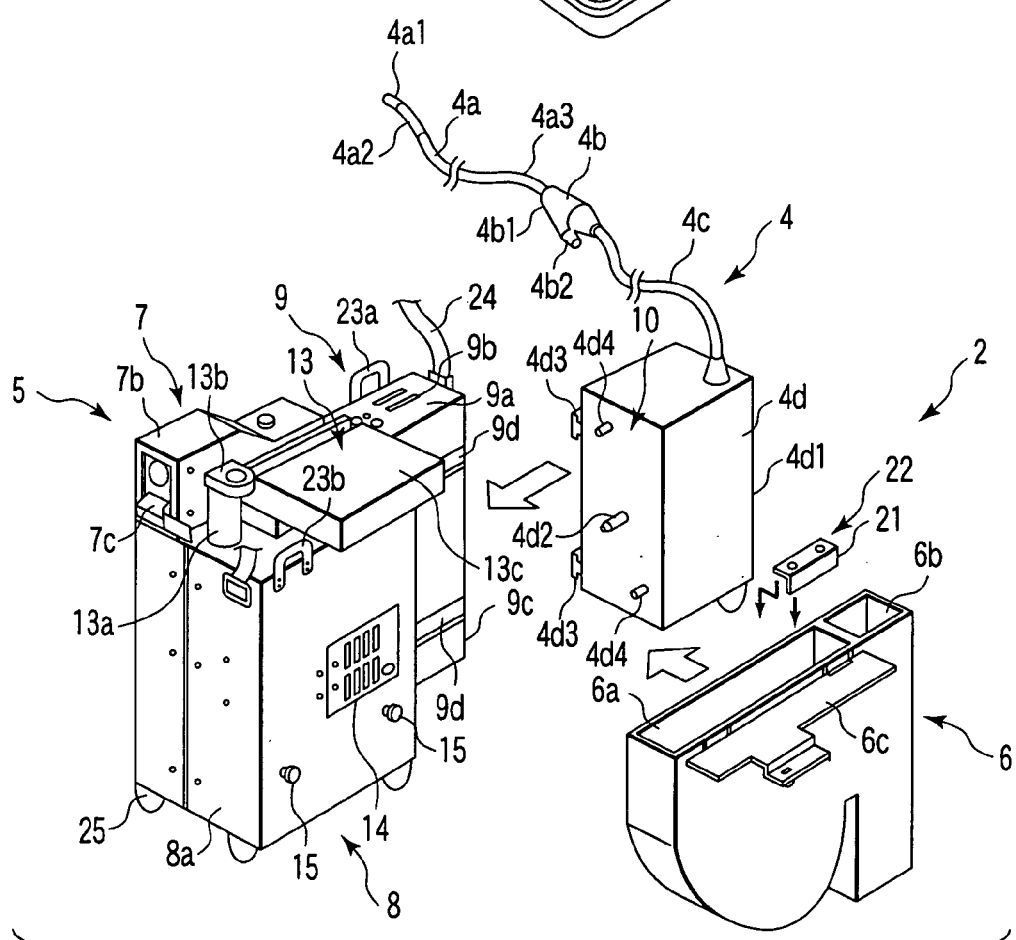
FIG. 2B is an exploded perspective view showing an assembling unit of an endoscope apparatus main body.

FIG. 2B is an exploded perspective view showing the assembling unit 2 of the endoscope apparatus 1.

At this assembling unit 2, a scope portion 4, a fixing unit 5, and a housing portion 6 are removably provided from each other.

Further, the scope portion 4 has an elongated insert portion 4a having flexibility, the insert portion being inserted into at least a space which is a target of inspection; an intermediate linking portion 4b; a universal cable 4c; and a base unit 4d (drive mechanism portion of the insert portion 4a). This insert portion 4a is disposed at the most distal end position, and is composed of: a head portion 4a1 having incorporated therein an observation optical system for observation, an illumination optical system and the like; a flexibly bending portion 4a2 which can be is flexibly bent remotely; and an elongated flexible tube portion 4a3. The flexibly bending portion 4a2 is provided between the head portion 4a1 and the flexible tube portion 4a3.

Figure 7:
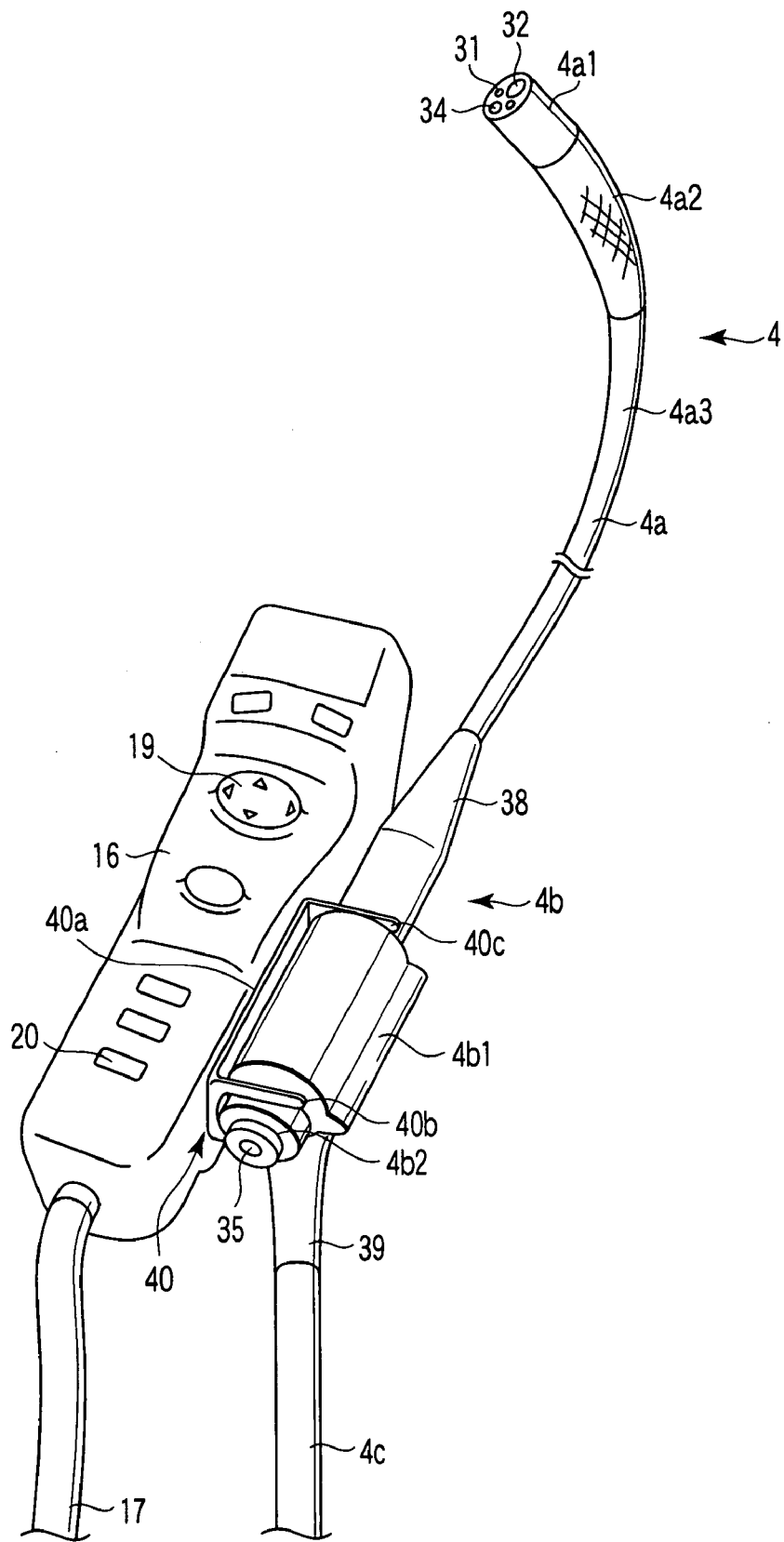
FIG. 7 is a perspective view showing a link state of the remote controller in the endoscope apparatus for industrial use and a grip portion of a scope portion according to the first embodiment.

On a distal end face of the head portion 4a1, as shown in FIG. 7, there are provided: an illumination window 31 for illumination optical system; an observation window 32 for observation optical system; an internal channel (manipulating device inserting channel) 33 provided at the inside of the insert portion 4a; and a distal opening end 34 (shown in FIG. 3), respectively.

Further, at the inside of the insert portion 4a, there are provided: a light guide (not shown) for transmitting illumination light to an illumination optical system; a signal line connected to a semiconductor image pickup device (such as CCD), for example, provided at the observation optical system; a flexibly bending wire for flexibly bending the flexibly bending portion 4a2; and the like, respectively.

Figure 3:
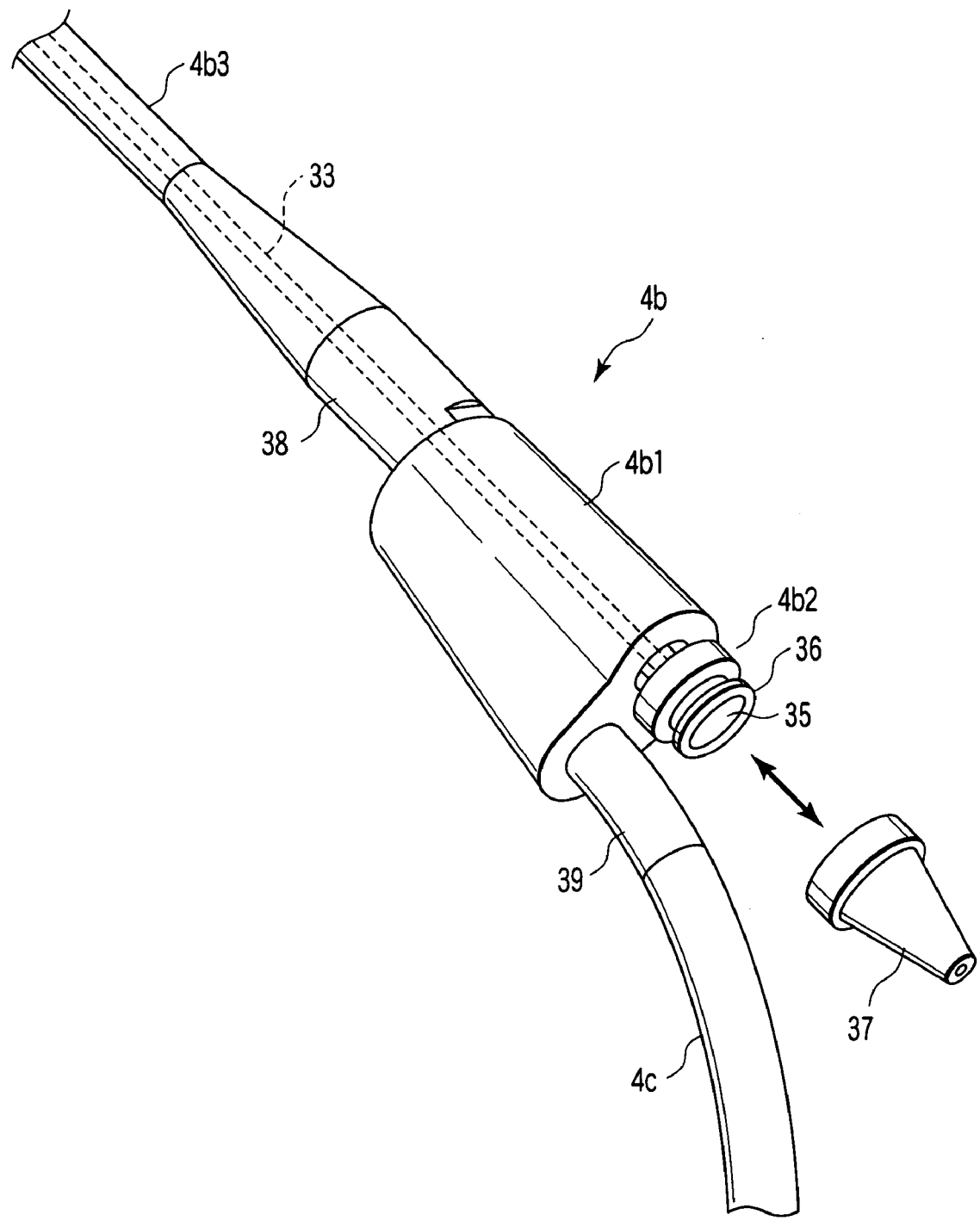
FIG. 3 is a perspective view showing a grip portion of a scope portion in the endoscope apparatus for industrial use according to the first embodiment.

A distal end part of the intermediate linking portion 4b is linked with a proximal end part o the flexible tube portion 4a3 of the insert portion 4a. As shown in FIG. 3, a grip portion 4b1 is provided at this intermediate linking portion 4b such that a user can grip by a single hand. A linking portion between a channel port section 4b2 and a distal end part of the universal cable 4c are provided in parallel at a read end part of the grip portion 4b1.

Here, at the channel port section 4b2, as shown in FIG. 4B, there is provided: a forceps opening (proximal opening end) 35 of the internal channel 33 extended along an axial direction at the inside of the insert portion 4a. A male screw portion 36 is formed at a marginal site of this forceps opening 35. A fixing bracket 37 of a hook type manipulating device described later is detachably screwed at this male screw portion 36.

A cylindrically shaped nut member 37a is provided at the fixing bracket 37 as shown in FIG. 5B. Then, a marginal site of the forceps opening 35 is inserted into the nut member 37a, and the nut member 37a is screwed at the male screw portion 36 of the forceps opening 35.

In addition, a cylindrically shaped fixing bracket 37b is provided at the inside of the nut member 37a. A tapered clamping portion 37a is provided at one end of the fixing device 37b. Further, a male screw portion 37d is formed on the outer periphery face of the fixing device 37b. A tightening nut 37e is screwed at this male screw portion 37d. A compression portion 37f formed in a tapered face shape is provided at the inside of the tightening nut 37e.

The tightening nut 37e is screwed into the male screw portion 37d of the fixing device 37b, whereby the compression portion 37f of the tightening nut 37e tightens the tightening portion 37c of the fixing bracket 37b. Therefore, a wire shaped manipulating device inserted into the fixing bracket 37 is fixed to be tightened by the tightening portion 37c.

As shown in FIG. 4B, a linking portion of the universal cable 4c is disposed in a state to be inclined diagonally with respect to an axial direction of the insert portion 4a. At the inside of this universal cable 4c, there are disposed: a light guide extended from the side of the insert portion 4a; a signal line for transmission of an image signal outputted from a CCD; a flexibly bending wire; and the like.

An insert portion protecting rubber 38 for preventing rapid bending of the insert portion 4a is provided at the distal end side of the intermediate linking portion 4b, and a universal cable rubber 39 for preventing rapid bending of the universal cable 4c is provided at the proximal end side thereof, respectively.

A proximal end part of the universal cable 4c is linked with the base unit 4d. This base unit 4d incorporates an electrically driven angle unit, an electrically driven angle board, a camera control unit, and the like which are not shown. Further, a flexibly bending wire in the insert portion 4a is linked with the electrically driven angle unit. This electrically driven angle unit incorporates a power unit such as a drive motor for driving the flexibly bending wire to be pulled. The flexibly bending wire is driven to be pulled by means of the electrically driven angle unit, and the flexibly bending portion 4a2 is remotely operated to be flexibly bent.

In addition, a signal line connected to the CCD disposed in the insert portion 4a is connected to the camera control unit. Then, image data on the endoscope observed image acquired by the CCD is converted into an electrical signal, and the converted image data is transmitted to the camera control unit via an electrical cable.

Moreover, as shown in FIG. 2B, a light guide connecting connector portion 4d2 is protruded on an end face of a unit case 4d1 of the base unit 4d. A proximal end part of a light guide (not shown) extended from the side of the universal cable 4c is linked with the light guide connector portion 4d2.

At a side plate of the unit case 4d1 of the base unit 4d, an upper and lower two-stepped protrusive attachment/detachment 4d3 for guiding movement of the base unit 4d during link with the fixing unit 5 is provided to extend along a substantially horizontal direction.

Further, at en end face of the unit case 4d1, a plurality of fixing brackets 4d4 are provided to be protruded. These fixing brackets 4d4 each are attached into a receptacle portion (not shown) at the side of the fixing unit 5, and is detachably linked. By this linking, a first connecting mechanism 10 between the base unit 4d and the fixing unit 5 is configured. The fixing unit 5 is composed of a power source portion 7, a light source device 8, and a recording unit 9. This power source portion 7, as shown in FIG. 3, is composed of a power source connector 7a, and a power source cover 7b, and a power source cable 7c is connected to the power source connector 7a.

In the recording unit 9, insert openings 9b for inserting a plurality of recording mediums, for example, memory card, is provided on a top face of a sheet metal based front panel 9a. On a side plate 9c of the recording unit 9, two upper and lower guide grooves 9d for guiding movement of the base unit 4d are provided along a substantially horizontal direction. The attachment/detachment 4d3 of the base unit 4d is removably mounted to be slid in these guide grooves 9d.

In addition, as shown in FIG. 2B, at the inside of a sheath cover 8a of the light source device 8, there are provided a lamp box having a light source lamp, a relay board, a lamp line board, an EL connector board, an IL switch, a ballast, a fan and the like which are not shown. A remote controller connector 11, a BNC connector 12, and a display device 13 are provided on a top face of the sheath cover 8a of the light source device 8. In this display device 13, for example, a liquid crystal display device (LCD monitor) 13c is mounted at the upper part of a cylindrically shaped mono-pad 13a via a hinge mechanism 13b. The CD monitor 13c is supported so as to enable upward and downward setting of the monitor by means of the hinge mechanism 13b.

At a side face of the sheath cover 8a of the light source device 8, a lamp replacing window 14 is provided as shown in FIG. 2B, and a plurality of mount pins 15 for mounting the housing portion 6 are provided.

The housing portion 6 is partitioned into a plurality of areas therein, for example, two large and small areas in the present invention. This housing portion is formed of: a scope housing box (insert portion housing portion) 6a partitioned as a large area; and a remote control housing portion (cable housing portion) 6b partitioned as a small area.

The scope housing box 6a houses the insert portion 4a of the scope portion 4, the intermediate linking portion 4b, and the universal cable 4c in a state to be bundled in a substantial ring shape. Further, a housing box lid 6c for opening and closing the scope housing box 6a is mounted on a top face of the housing portion 6.

In addition, a remote controller (input device) 16 for operating the base unit 4d of the scope portion 4 and a flexible cable 17 at one end connected to the remote controller 16 are housed in the remote housing portion 6b. Here, a connector (not shown) is connected to the other end of the case 17. The connector is detachably connected to the remote controller connector 11.

Further, on a mount face for the side of the fixing unit 5 in the housing portion 6, a pin insert hole (not shown) is formed at a position corresponding to the mount pin 15 of the light source device 8. The mount pin 15 is inserted into the pin insert hole, and the housing portion 6 is removably mounted on a side face of the sheath cover 8a of the light source device 8.

A substantial L-shaped scope housing box pressing member 21 is fixed on a side face of the housing portion 6 at the sheath cover 8a side. When the housing portion is mounted, this member is fixed to be screwed at the side of the fixing unit 5. The scope housing box pressing member 21 configures a second connecting mechanism 22 for fixing the housing portion 6 to the sheath cover 8a.

Further, in the endoscope apparatus 1 according to the present embodiment, when the assembling unit 2 is retracted from the endoscope housing case 3, two available grips 23a, 23b and a shoulder strap 24 are provided. Among them, the grip 23a is mounted at the upper part of the recording unit 9 in of the recording unit 5, and the other grip 23b is mounted at the upper part of the sheath cover 8a of the light source device 8, respectively.

Similarly, one end of the shoulder strap 24 is fixed at the upper part of the recording unit 9 in the fixing unit 5, and the other end is fixed at the upper part of the sheath cover 8a of the light source device 8, respectively. A plurality of rubber legs 25 are fixed at the bottom of the assembling unit 2.

Figure 6A:
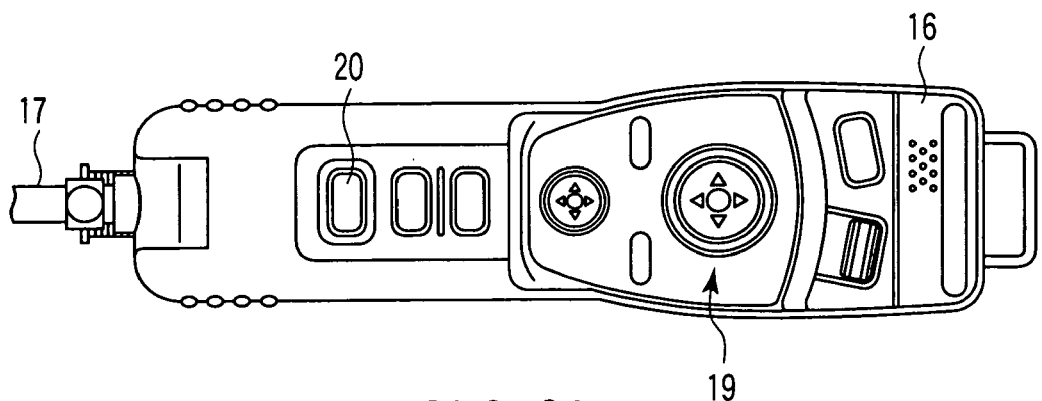
FIG. 6A is a plan view showing a remote controller in the endoscope apparatus for industrial use according to the first embodiment.
Figure 6B:
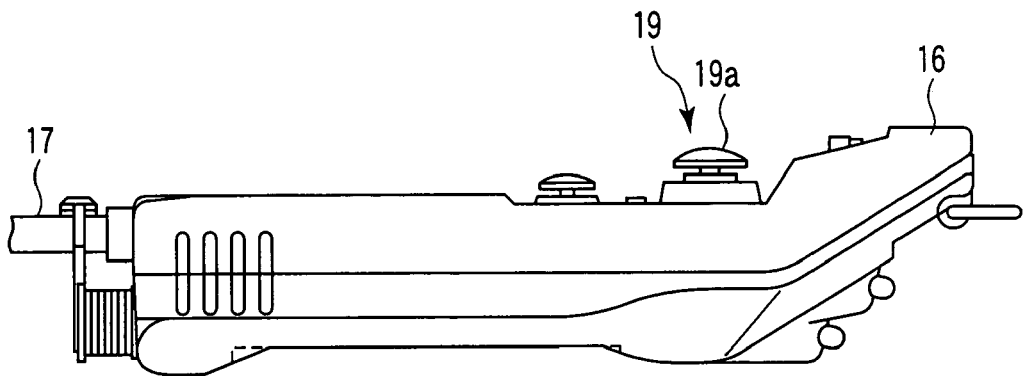
FIG. 6B is a side view of the remote controller.

Now, an exemplary configuration of the remote controller 16 will be described with reference to FIGS. 6A to 6C.

The remote controller 16 has a joystick (flexibly bending operation portion) 19 and a power button 20, the joystick serving as an instruction input portion for remotely operating at least the flexibly bending direction of the flexibly bending portion 4a2 of the scope portion 4 to be bend in the vertical and horizontal directions.

Figure 6C:
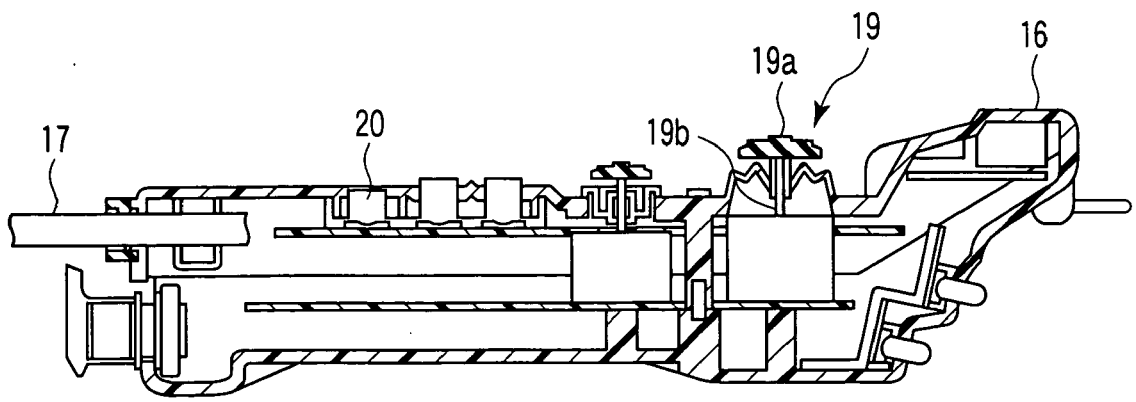
FIG. 6C is a longitudinal cross section of the remote controller.

The joystick 19 has an operating lever 19a which is turnably supported around a fulcrum 19b as shown in FIG. 6C, and generates a signal corresponding to a tilt angle of the operating lever 19a.

As shown in FIG. 7, a fixing bracket (linking portion) 40 for removably mounting the intermediate linking portion 4b can be mounted on a side face of the remote controller 16. The fixing bracket 40 is formed in a U-shape, and is composed of: a base plate 40a for fixing the remote controller on one side face; and attaching portions 40b, 40c erected at a substantially right angle from both ends thereof. Further, this fixing bracket is formed at the attaching portions 40b, 40c in a substantial U-shape for mounting the remote controller on the intermediate linking portion 4b.

The grip portion 4b1 of the intermediate linking portion 4b is plugged into each of these attaching portions 40b and 40c, whereby the remote controller 16 and intermediate linking portion 4b can be linked integrally with each other. As shown in FIG. 7, in this integrally linked state, the opening direction of the forceps opening 35 of the channel port section 4b2 is on the side of the cable 17 of the remote controller 16.

According to this linking, a position is set such that an operating range of the joystick 19 and a work of inserting the internal channel 33 into the forceps opening 35 do not interfere with each other. The channel port section 4b2 can be mounted on either of the left and right side faces of the remote controller 16.

Now, an operation of the thus configured endoscope apparatus for industrial use will be described here.

The endoscope apparatus 1 for industrial use according to the present embodiment includes the assembling unit 2 having the scope portion 4, the fixing unit 5, and the housing portion 6 integrally assembled with each other. The endoscope apparatus is housed in the endoscope housing case 3 as shown in FIG. 1 (the lid 3b is in a closed state). In general, the endoscope housing case 3 is transported near a place targeted for inspection.

Then, the lid 3b of the endoscope housing case 3 is opened, and the assembling unit 2 is taken out, and the scope portion 4 and the remote controller 16, the scope portion being housed to be looped, are taken out from the housing portion 6 by opening a housing box lid 6c. The looped scope portion 4 is extended, the insert portion 4a is inserted into a space which is a target of inspection, and endoscope inspection in the space targeted for inspection is carried out.

In the case where there is no need to rigidly protect the assembling unit 2 at the time of transport, the assembling unit may be transported to a required place in its original state without being housed in the endoscope housing case 3. The assembling unit 2 is designed such that the fixing unit 5, the base unit 4d, and the housing portion 6 have sufficient strengths, respectively.

Further, the assembling unit 2 itself may be transported by hanging a shoulder belt on the shoulder or loading the assembling unit 2 on a trolley. The scope portion 4 (insert portion 4a, intermediate linking portion 4b, and universal cable 4c) and the remote controller 16 are placed in a state of being housed in the housing portion 6.

When endoscope inspection in a space which is a target of inspection is carried out, an AC cable (not shown) is plugged into a receptacle, and the remote controller 16 and the cable 17 are taken out from the remote controller housing portion 6b. Then, the scope portion 4 (insert portion 4a, intermediate linking portion 4b, and universal cable 4c) is taken out from the scope housing box 6a, and the power button 20 of the remote controller 16 is turned ON.

Figure 8:
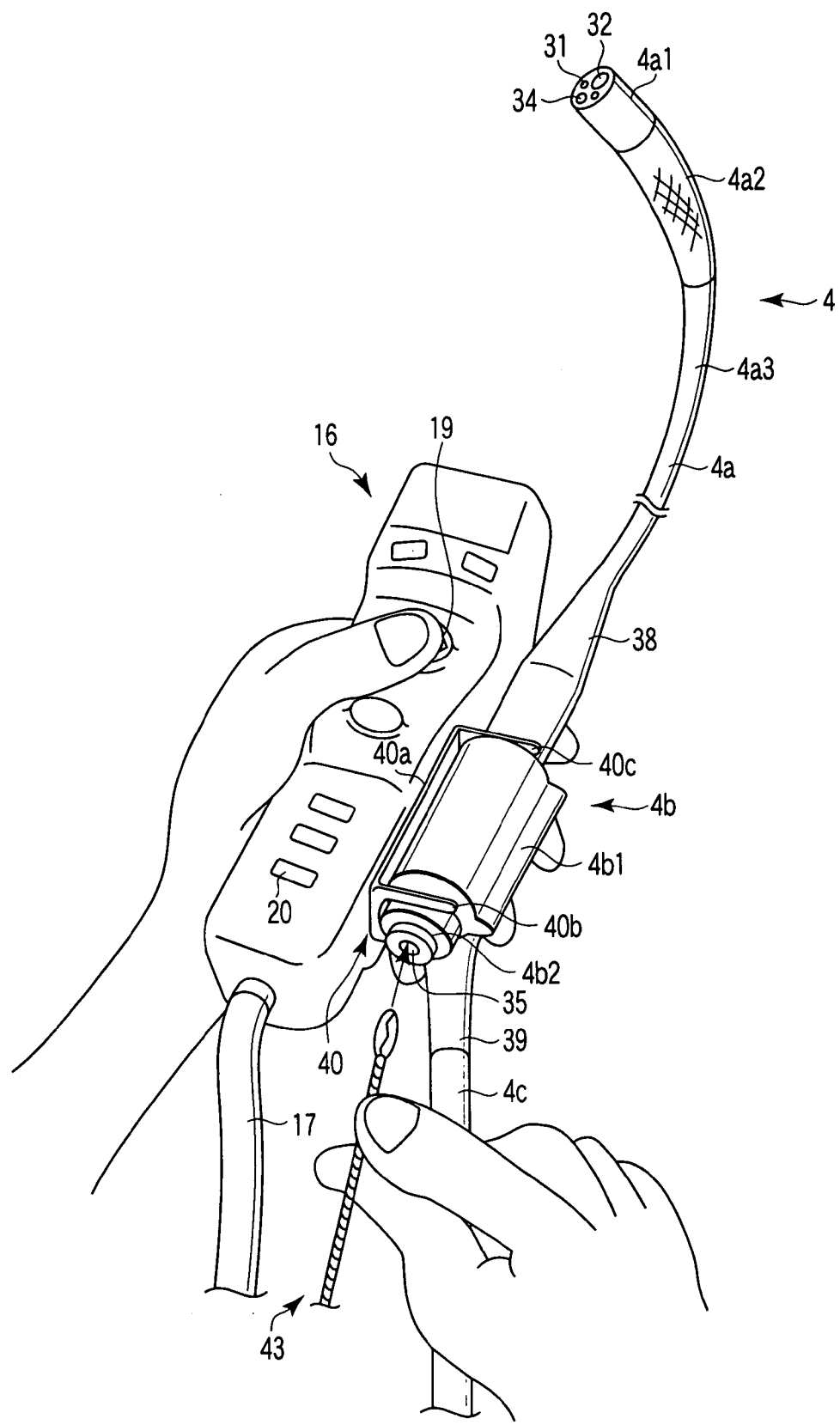
FIG. 8 is a perspective view showing a state in which the forceps is inserted into the forceps opening of the grip portion in the endoscope apparatus for industrial use according to the first embodiment.
Figure 9:
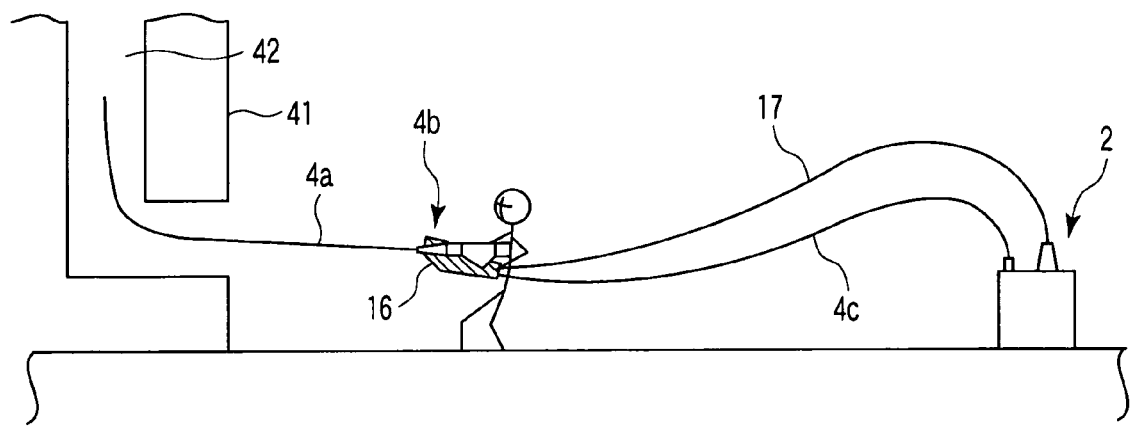
FIG. 9 is a schematic view showing a use state of the endoscope apparatus for industrial use according to the first embodiment.

After the remote controller has been turned ON, as shown in FIG. 9, the insert portion 4a of the scope portion 4 is inserted into a space 42 targeted for inspection of an object 41 such as a turbine. At this time, as shown in FIG. 7, the remote controller 16 and the intermediate linking portion 4b may be used in a state in which they are linked with each other in advance. In this case, as shown in FIG. 8, for example, one grips the remote controller 16 by the left hand, and operates the joystick 19 by the thumb of the left hand.

In the case of using a manipulating device 43 such as a forceps, as shown in FIG. 8, one makes an operation of inserting the manipulating device 43 into the forceps opening 35 of the channel port section 4b2 by the right hand. At this time, as shown in FIG. 7, the opening direction of the forceps opening 35 of the channel port section 4b2 is disposed at the opposite side of the joystick 19. Thus, the flexibly bending operation by the left hand and an operation of the manipulating device 43 by the right hand do not interfere with each other. An operation of the joystick 19 by the left hand and an operation of the manipulating device 43 by the right hand can be easily carried out, respectively.

Figure 10:
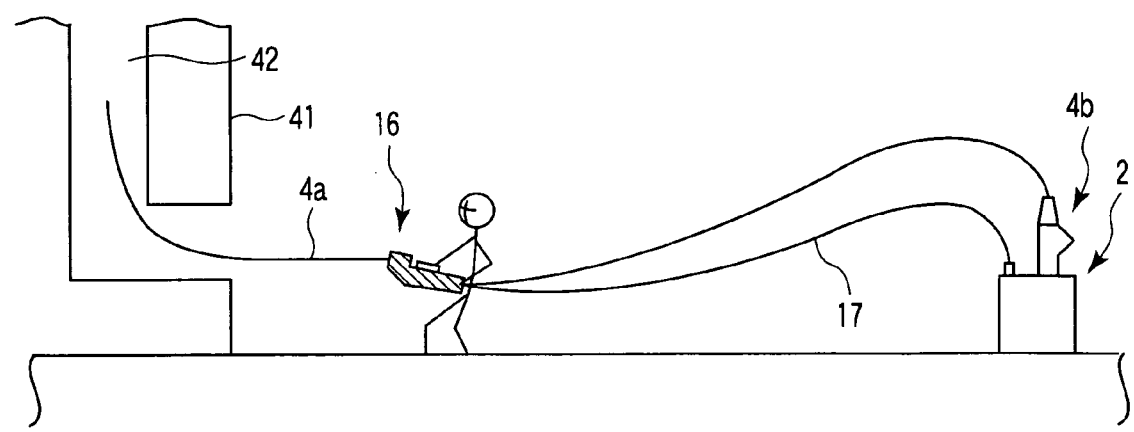
FIG. 10 is an illustrative view for illustrating a work of carrying out only a flexibly bending operation of a flexibly bending portion when the endoscope apparatus for industrial use according to the first embodiment is used.

In the case where there is no need to use the manipulating device 43 such as a forceps, the intermediate linking portion 4b is pulled out in advance from the fixing bracket 40 of the remote controller 16; and as shown in FIG. 10, the remote controller 16 and the intermediate linking portion 4b of the scope portion 4 may be used separately. In this case, as shown in FIG. 11, for example, one carries out inspection by gripping the remote controller 16 by a single hand, and gripping an arbitrary position between the insert portion 4a, intermediate linking portion 4b, and universal cable 4c, for example, an intermediate position of the insert portion 4a.

The operation of the manipulating device 43 can be carried out even in a state in which the remote controller 16 and the intermediate linking portion 4b of the scope portion 4 are separated from each other. In this case, as shown in FIG. 12, for example, an operation for inserting the manipulating device 43 into the forceps opening 35 of the channel port section 4b2 by the right hand is carried out in a state in which the intermediate linking portion 4b of the scope portion 4 is gripped by the left hand.

Figure 13:
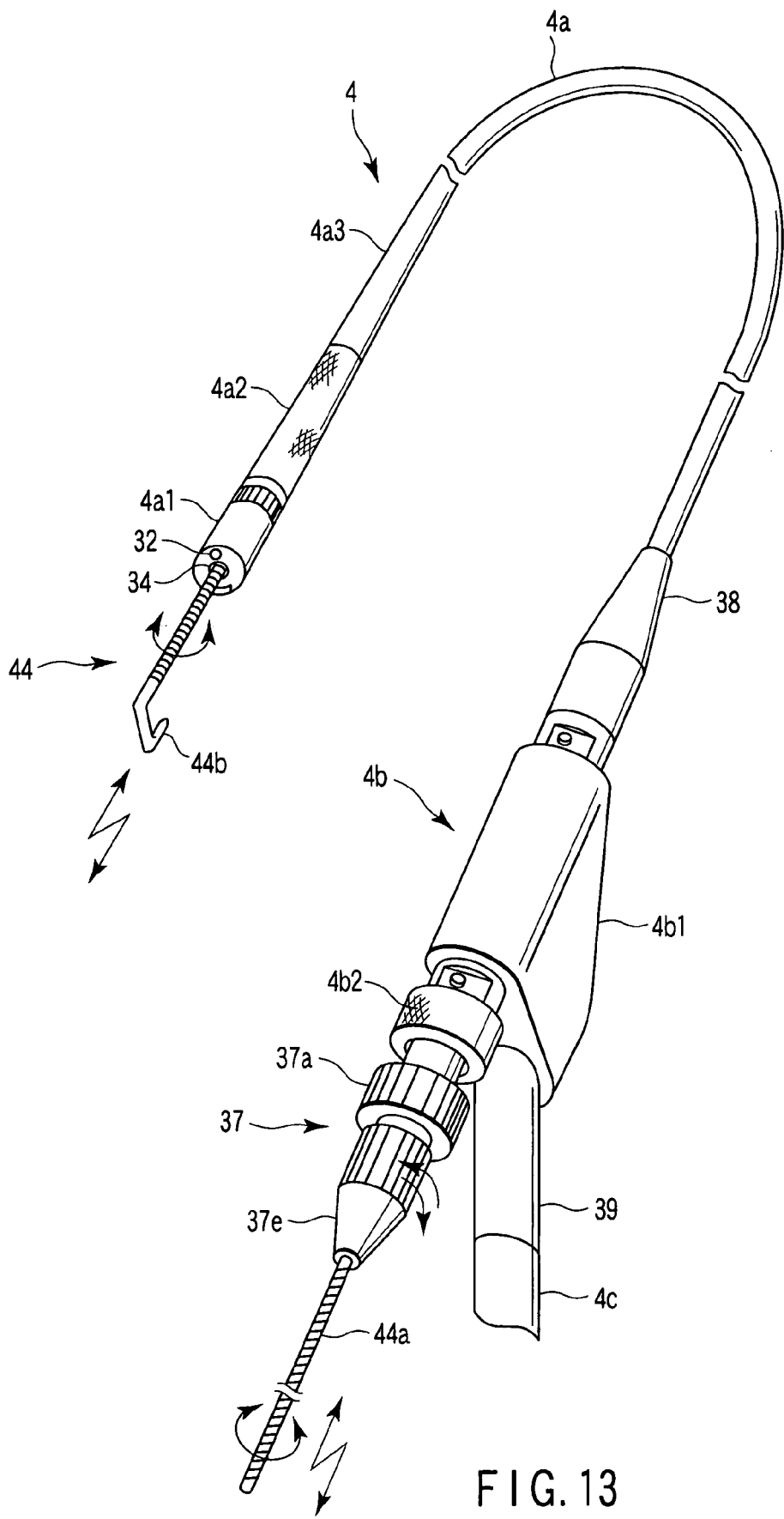
FIG. 13 is an illustrative view for illustrating a work of inserting a hook type manipulating device into an internal channel and fixing the device at the forceps opening of the grip portion in the endoscope apparatus for industrial use according to the first. embodiment.

In addition, as shown in FIG. 13, in the case of using a hook type manipulating device 44 in which a substantially U-shaped hook portion 44b is fixed at a distal end part of an elongated flexible operating wire 44a, the hook type manipulating device 44 is set to the internal channel 33 of the insert portion 4a of the scope portion 4 in accordance with the following operating procedures. That is, a proximal end part of the operating wire 44a of the hook type manipulating device 44 is inserted into the distal opening end 34 of a head portion 4a1 at the insert portion 4a. At this time, the operating wire 44a of the hook type manipulating device 44 is folded back to the side of the intermediate linking portion 4b of the insert portion 4a through the inside of the internal channel 33 of the insert portion 4a.

Further, when the hook type manipulating device 44 is used, the nut member 37a of the fixing bracket 37 is screwed in advance at the male screw portion 36 of the channel port section 4b2. Then, through the inside of the internal channel 33 of the insert portion 4a, the operating wire 44a extended to the side of the intermediate linking portion 4b of the insert portion 4a passes through the inside of the fixing bracket 37 from the forceps opening 35 of the channel port section 4b2, and is pulled out to the outside.

Thereafter, the tightening nut 37e is screwed into the male screw portion 37d, whereby the tightening portion 37c is compressed so as to be tightened inwardly by the compression portion 37f. Namely, the operating wire 44a is fixed after tightened by the tightening portion 37c. In this manner, the hook portion 44b is fixed at the distal opening end 34 of the head portion 4a1.

Figure 14:
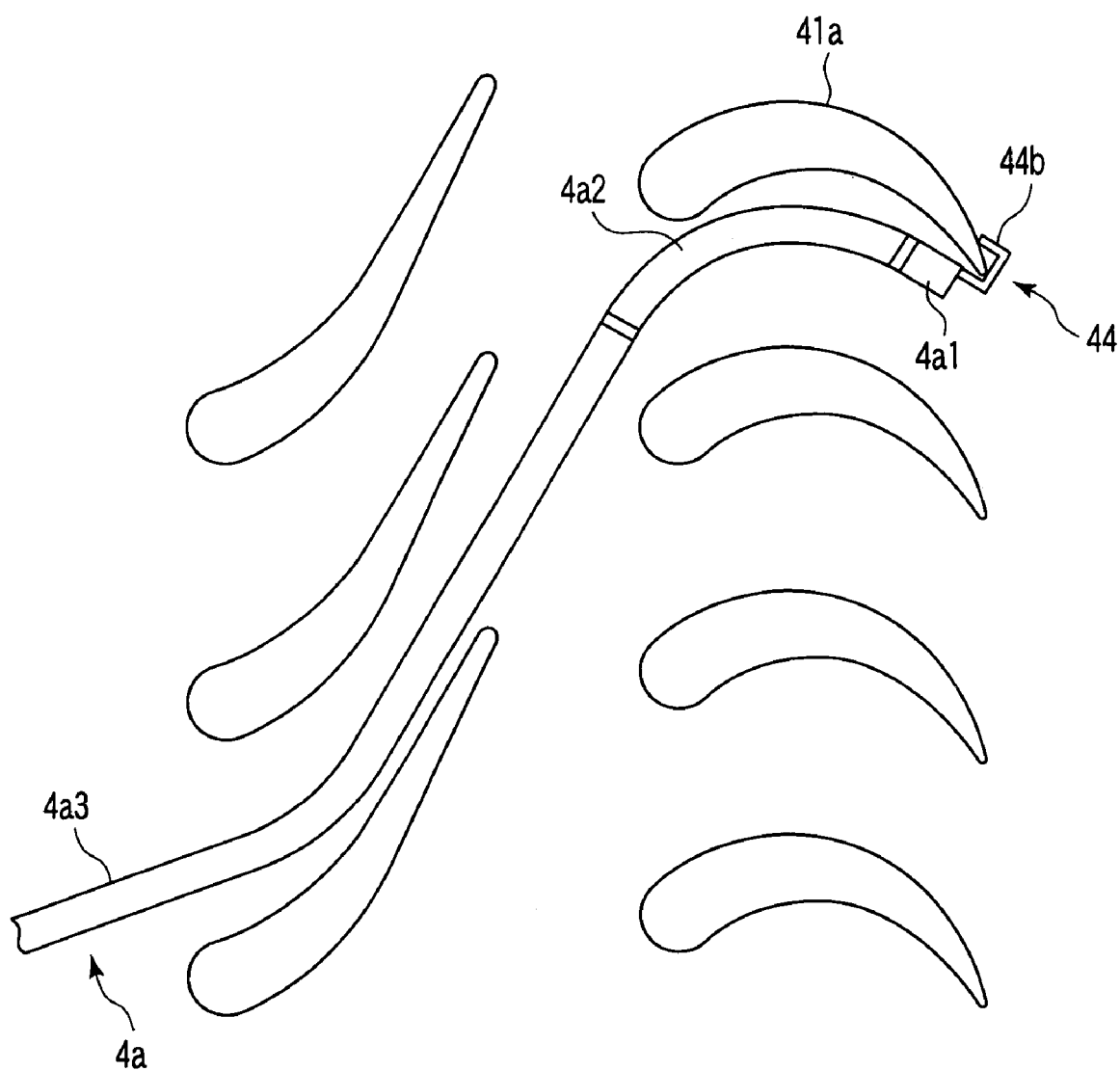
FIG. 14 is an illustrative view for illustrating a state in which a hook portion of the hook type manipulating device is attached in an engine when the endoscope apparatus for industrial use according to the first embodiment is used.

Subsequently, the insert portion 4a of the scope portion 4 is inserted into the space 42 targeted for inspection of the object 41 such as a turbine. Then, as shown in FIG. 14, the hook portion 44b of the hook type manipulating device 44 is attached in a state in which the hook portion is hooked at a marginal portion such as a blade 41a in the space 42 targeted for inspection of the object 41. In this state, endoscope inspection in the space 42 targeted for inspection is carried out.

After the endoscope inspection in the space 42 targeted for inspection, the remote controller 16 is housed in the remote controller housing portion 6b in a state in which the power button 20 is turned OFF. Further, the insert portion 4a of the scope portion 4 used in endoscope inspection, the intermediate linking portion 4b, and the universal cable 4c are bundled in a substantially ring shape, and are housed in the scope housing box 6a. In this manner, the housing of constituent devices of the endoscope apparatus 1 for industrial use has now been completed.

Then, in the case where transport by airplane or truck is utilized in order to use the endoscope apparatus 1 for industrial use at a remote site, the assembling unit 2 may be housed in the endoscope housing case 3. In the other case, the endoscope apparatus may be used in a state in which the assembling unit 2 is removed from the endoscope housing case 3.

The following advantageous effect is achieved with the above described configuration.

The endoscope apparatus 1 for industrial use according to the present invention comprises: the intermediate linking portion 4b of the scope portion 4; and the fixing bracket 40 for establishing a detachable link with the remote controller 16. Therefore, when there is no need to use the manipulating device 43 such as a forceps, the intermediate linking portion 4b is pulled out in advance from the fixing bracket 40 of the remote controller 16, whereby the remote controller 16 and the intermediate linking portion 4b of the scope portion 4 can be used to be separated from each other as shown in FIG. 10. In this case, the input operation by the joystick 19 of the remote controller 16 and the manipulating device operation from the endoscope opening 35 of the channel port section 4b2 can be carried out independently, respectively.

When the intermediate linking portion 4b of the scope portion 4 is linked with the remote controller 16, the opening direction of the forceps 35 of the channel port section 4b2 is oriented to be opposite to the joystick 19. Therefore, an operation of the joystick 19 by the left hand and an operation of the manipulating device 43 by the right hand do not interfere with each other, so that the respective operations can be easily carried out.

Figure 15:
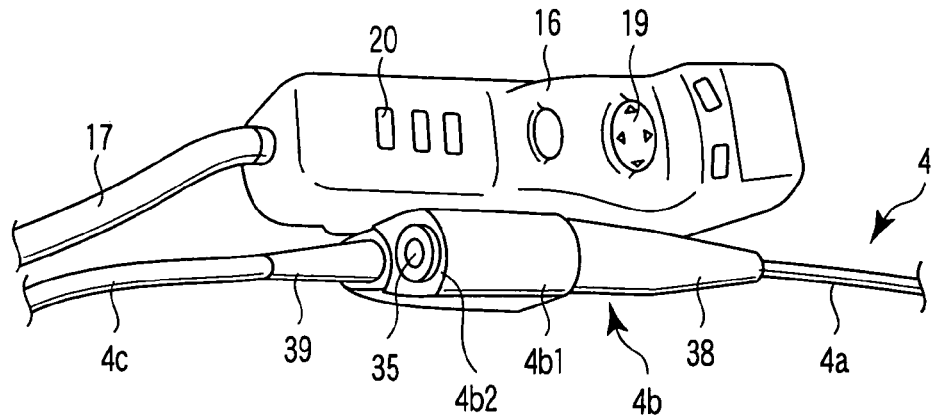
FIG. 15 is a perspective view of essential portions showing a first modified example of a state of a link between the remote controller and the grip portion of the scope portion in the endoscope apparatus for industrial use according to the first embodiment.

FIG. 15 is a perspective view showing essential portions at which a link state between the remote controller 16 and the intermediate linking portion 4b of the scope portion 4 in the endoscope apparatus 1 for industrial use according to the first embodiment is deformed as a first modified example.

In this modified example, the intermediate linking portion 4b is configured to be mounted on a side face of the remote controller 16 such that the universal cable 4c and the cable 17 are placed in parallel to each other. The opening direction of the forceps portion 35 of the channel port section 4b2 is disposed to be in a diagonally upward direction from an operating face of the remote controller 16.

With such a configuration, in the case where both of the flexibly bending operation of the flexibly bending portion by operation of the joystick 19 and the forceps operation from the forceps opening 35 of the channel port section 4b2 are carried out at the same time, it is possible to visually check the joystick 19 and forceps opening 35 simultaneously. Thus, such operations can be carried out more easily and reliably.

Figure 16:
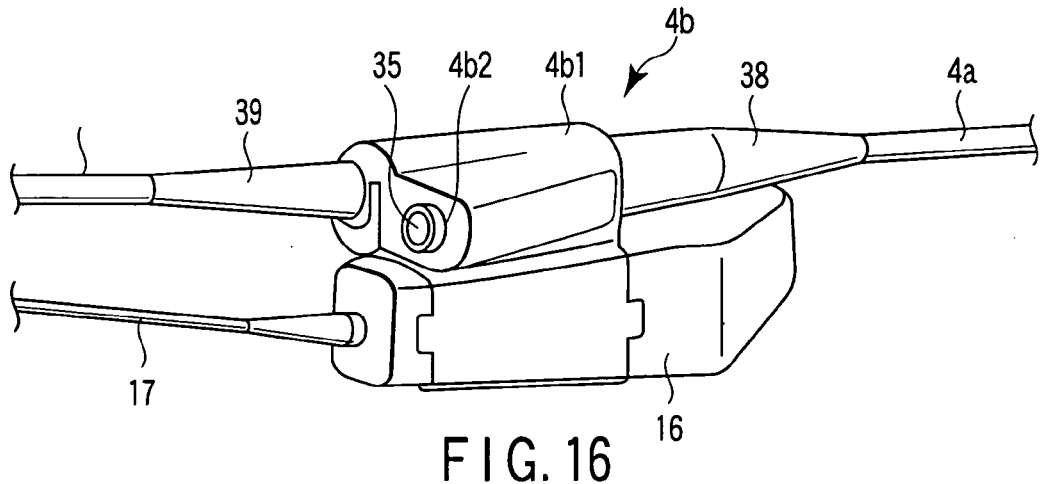
FIG. 16 is a perspective view of essential portions showing a second modified example of a state of a link between the remote controller and the grip portion of the scope portion in the endoscope apparatus for industrial use according to the first embodiment.

FIG. 16 is a perspective view showing essential portions at which a link state between the remote controller 16 and the intermediate linking portion 4b of the scope portion 4 in the endoscope apparatus 1 for industrial use according to the first embodiment is deformed as a second modified example.

In this modified example, the universal cable 4c and the cable 17 are placed in parallel to each other; the intermediate linking portion 4b is configured to be mounted on the remote controller 16 such that the forceps opening 35 reaches a back face side of the remote controller 16; and the opening direction of the forceps opening 35 is disposed diagonally downwardly at the opposite side of the joystick 19.

According to the present modified example, in the case where both of the flexibly bending operation of the flexibly bending portion by operation of the joystick 19 and the forceps operation from the forceps opening 35 of the channel port section 4b2 are carried out at the same time, it is possible to visually check the joystick 19 and forceps opening 35 at the same time. Thus, such operations can be carried out more easily and reliably.

Figure 17:
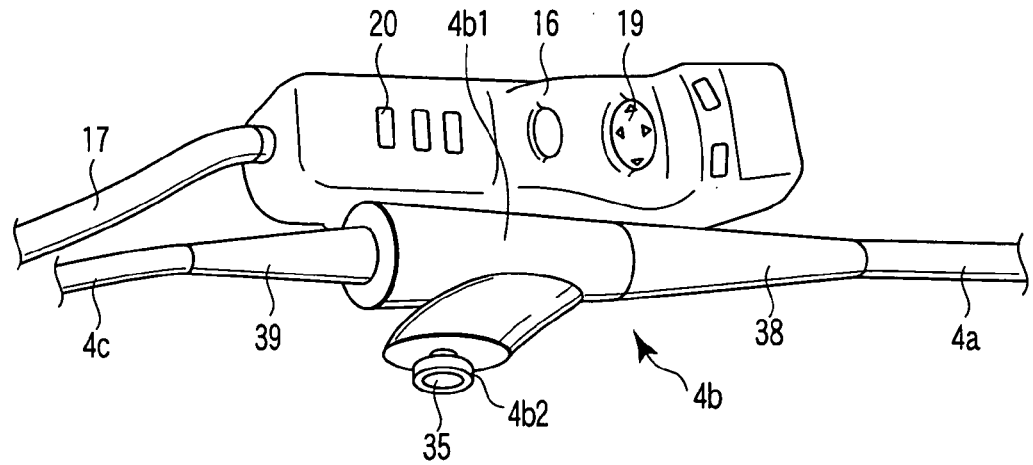
FIG. 17 is a perspective view of essential portions showing a third modified example of a state of a link between the remote controller and the grip portion of the scope portion in the endoscope apparatus for industrial use according to the first embodiment.

In addition, FIG. 17 is a perspective view showing essential portions at which a link state between the remote controller 16 and the intermediate linking portion 4b of the scope portion 4 in the endoscope apparatus 1 for industrial use according to the first embodiment is deformed as a third modified example. This modified example is provided as an example of using a scope portion provided such that the opening direction of the forceps opening 35 is outwardly oriented diagonally backwardly. Namely, when the intermediate link portion 4b is linked with a side face of the remote controller 16, the forceps opening 35 of the scope portion 4 is outwardly oriented diagonally backwardly.

According to the present modified example, an operation of the joystick 19 by the left hand and an operation of the manipulating device 43 by the right hand do not interfere with each other. As a result, the input operation by the joystick 19 of the remote controller 16 and the manipulating device operation from the forceps opening 35 of the channel port section 4b2 do not interfere with each other, so that their respective operations can be easily carried out.

FIGS. 18 to FIGS. 20A and 20B each show a configuration of essential portions of an endoscope apparatus 1 for industrial use according to a second embodiment of the present invention. In the present embodiment, a configuration of a link portion between the intermediate linking portion 4b of the scope portion 4 and the remote controller 16 in the previously described endoscope apparatus 1 for industrial use according to the first embodiment (refer to FIGS. 1 to 14) has been changed as follows. In the present embodiment, a basic configuration of the endoscope apparatus 1 for industrial use is substantially similar to that according to the first embodiment. Thus, like elements in the first embodiment are designated by like reference numerals. A duplicate description is omitted here.

Figure 19B:
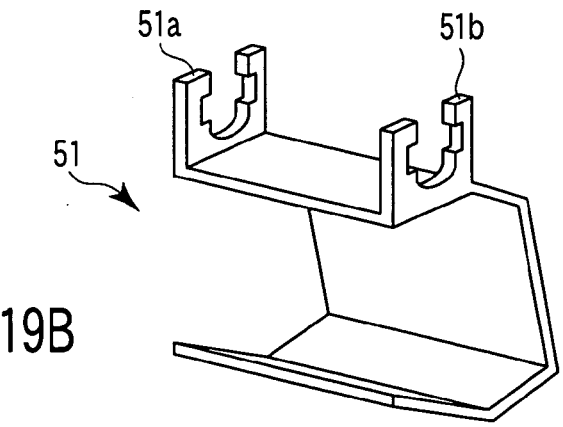
FIG. 19B is a perspective view showing a linking member mounted on the remote controller.
Figure 19A:
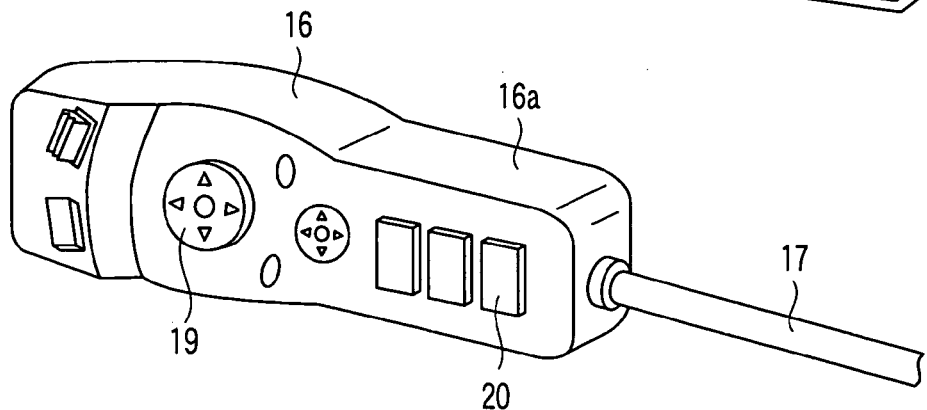
FIG. 19A is a perspective view showing a remote controller of the endoscope apparatus for industrial use according to the second embodiment.

In the present embodiment, a sheet-spring-shaped connecting device 51 flexibly bent in a substantial U-shape is provided, the connecting device being removably mounted on the main body 16a of the remote controller 16. As shown in FIG. 19B, substantially U-shaped attaching portions 51a, 51b are provided at both ends on a side wall face of one side of the connecting device 51 so as to be erected at a substantial right angle.

Figure 18:
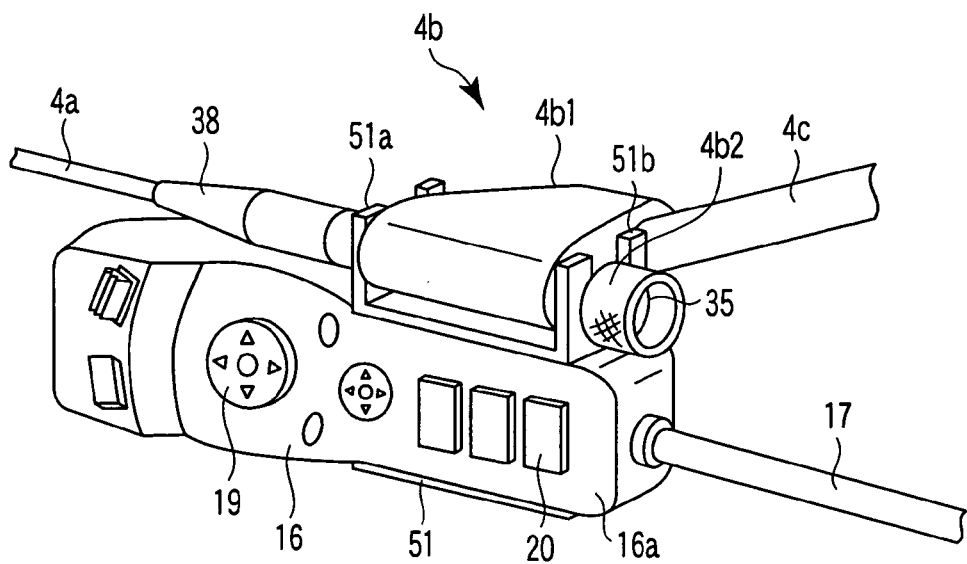
FIG. 18 is a perspective view showing a configuration of essential portions in an endoscope apparatus for industrial use according to a second embodiment of the present invention.
Figure 20B:
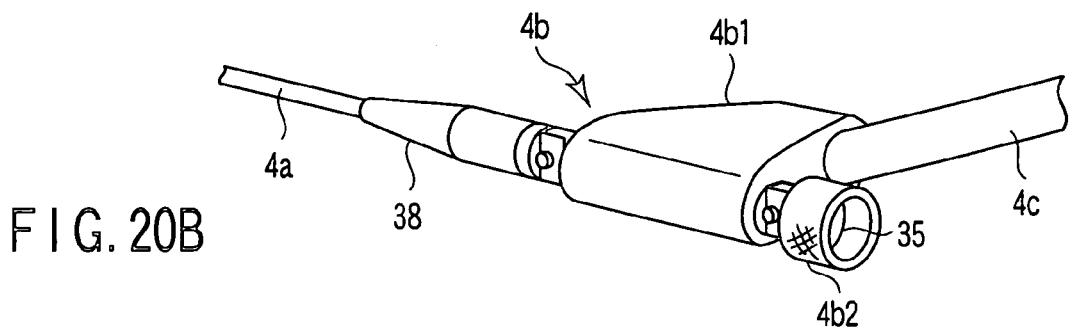
FIG. 20B is a perspective view showing a linking portion between a proximal end part of an insert portion and a universal cable.
Figure 20A:
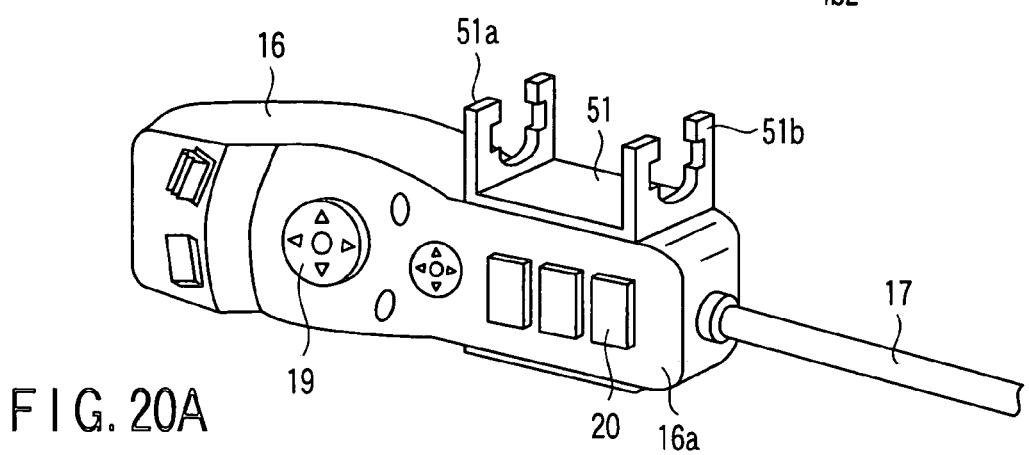
FIG. 20A is a perspective view showing a state in which the linking member is mounted on the remote controller of the endoscope apparatus for industrial use according to the second embodiment.

In the present embodiment, as shown in FIG. 20A, the connecting device 51 is mounted in advance at the side of the power button 20 of the remote controller 16. The intermediate linking portion 4b of the scope portion 4 shown in FIG. 20B is plugged into the attaching portions 51a, 51b of the connecting device 51, and is mounted as shown in FIG. 18. The connecting device 51 can be mounted on either of the right and left of the remote controller 16.

In the present embodiment, the connecting device 51 is attached with the main body 16a of the remote controller 16. Further, the intermediate linking portion 4b of the scope portion 4 can be mounted to be plugged into the attaching portions 51a, 51b of the connecting device 51.

In this mount state, the opening direction of the forceps opening 35 of the channel port section 4b2 is disposed at the opposite side of the joystick 19. Therefore, an operation of the joystick 19 by the left hand and an operation of the manipulating device 43 by the right hand do not interfere with each other, so that their respective operations can be easily carried out.

In the present embodiment as well, when there is no need to use the manipulating device 43 such as a forceps, the intermediate linking portion 4b is pulled out in advance from the connecting device 51 of the remote controller 16, whereby the remote controller 16 and the intermediate linking portion 4b of the scope portion 4 can be used to be separated from each other. Therefore, in the present embodiment as well, there is an advantageous effect that the usability of the endoscope apparatus 1 for industrial use can be improved.

Figure 21:
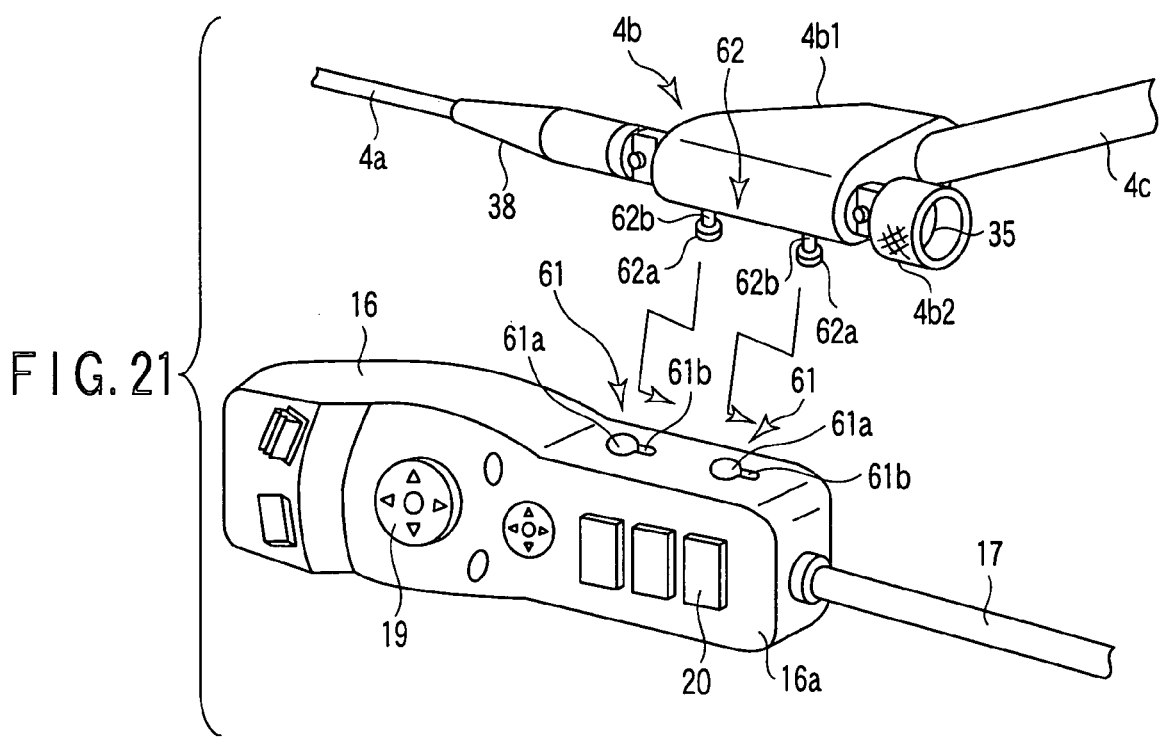
FIG. 21 is a perspective view showing a configuration of essential portions in an endoscope apparatus for industrial use according to a third embodiment of the present invention.

FIG. 21 shows a configuration of essential portions of an endoscope apparatus 1 for industrial use according to a third embodiment of the present invention. In the present embodiment, a configuration of a linking portion of the intermediate linking portion 4b with the remote controller 16 has been changed.

In the present embodiment, a plurality of, for example, two attaching holes 61 are provided at one side wall part of the main body 16a of the remote controller 16. These attaching holes 61 are formed such that a large diameter hole 61a and an attaching groove 61b whose groove width is smaller than a diameter of the large diameter hole 61a are connected with each other.

Further, at a side face of a grip portion 4b1, there are provided two attaching protrusions (bolt shaped) including a top portion (slip proof portion) 62a attached with the attaching hole 61; and a body portion (attaching pin) 62b capable of passing the attaching groove 61b. These top portions 62a are attached with the attaching hole 61 to slide the attaching groove 61b in a horizontal direction, and is attached to abut against a groove wall. Then, the scope portion 4 is directly linked with the main body 16a of the remote controller 16. Although two attaching holes and two attaching protrusions each are provided in the present embodiment, the number of them is not limited thereto.

In addition, each of the attaching protrusions is pulled out by being slid from the attaching groove 61b of the remote controller 16, and the remote controller 16 and scope portion 4b can be separated from each other, and can be attachably/detachably used. The opening direction of the forceps opening 35 when the scope portion 4 and the remote controller 16 are linked with each other is oriented to the side of the cable 17. An operation of the joystick 19 by the left hand and an operation of the manipulating device 43 by the right hand do not interfere with each other, and thus, these operations can be easily carried out, respectively.

Moreover, in the present embodiment as well, when there is no need to use the manipulating device 43 such as a forceps, each of the attaching protrusions 62 of the scope portion 4 is pulled out from each of the attaching holes 61 of the remote controller 16, whereby the remote controller 16 and the intermediate linking portion 4b of the scope portion 4 can be used to be separated from each other. Therefore, in the present embodiment as well, there is an advantageous effect that the usability of the endoscope apparatus 1 for industrial use can be improved.

Figure 22:
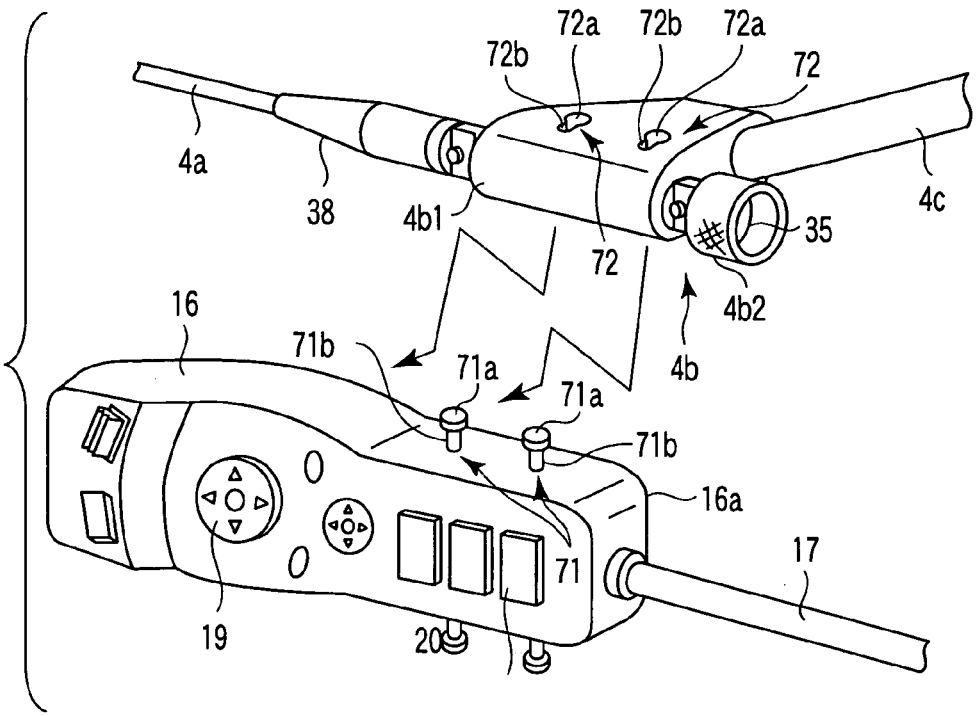
FIG. 22 is a perspective view showing a configuration of essential portions in an endoscope apparatus for industrial use according to a fourth embodiment of the present invention.

FIG. 22 shows a configuration of essential portions of an endoscope apparatus 1 for industrial use according to a fourth embodiment of the present invention.

In the present embodiment, a configuration of the linking portion between the intermediate linking portion 4b of the scope portion 4 and the remote controller 16 has been changed as follows.

In the present embodiment, an attaching hole and an attaching protrusion which are similar to those described previously are used. For example, this configuration is such that two attaching protrusions 71 are provided at the side wall portions on both sides of the main body 16a of the remote controller 16, and attaching holes are provided respectively on both side faces of the grip portion 4b1.

In this configuration, the attaching holes and attaching protrusions are formed on both side faces of each of the main body 16a and grip portion 4b1, thus making it possible to establish a link with either of them according to the usability. Moreover, each of the attaching protrusions 71 of the remote controller 16 is pulled out from each of the attaching holes 72 of the grip portion 4b1 of the intermediate linking portion 4b, whereby the remote controller 16 and the intermediate linking portion 4b of the scope portion 4 can be used to be separated from each other. Therefore, in the present embodiment as well, there is an advantageous effect that the usability of the endoscope apparatus 1 for industrial use can be improved.

Also in the present embodiment, the opening direction of the endoscope opening 35 when the scope portion 4 and the remote controller 16 are linked with each other is oriented to the side of the cable 17. The operation of the joystick 19 by the left hand and the operation of the manipulating device by the right hand do not interfere with each other, so that these operations can be easily carried out, respectively.

Figure 23:
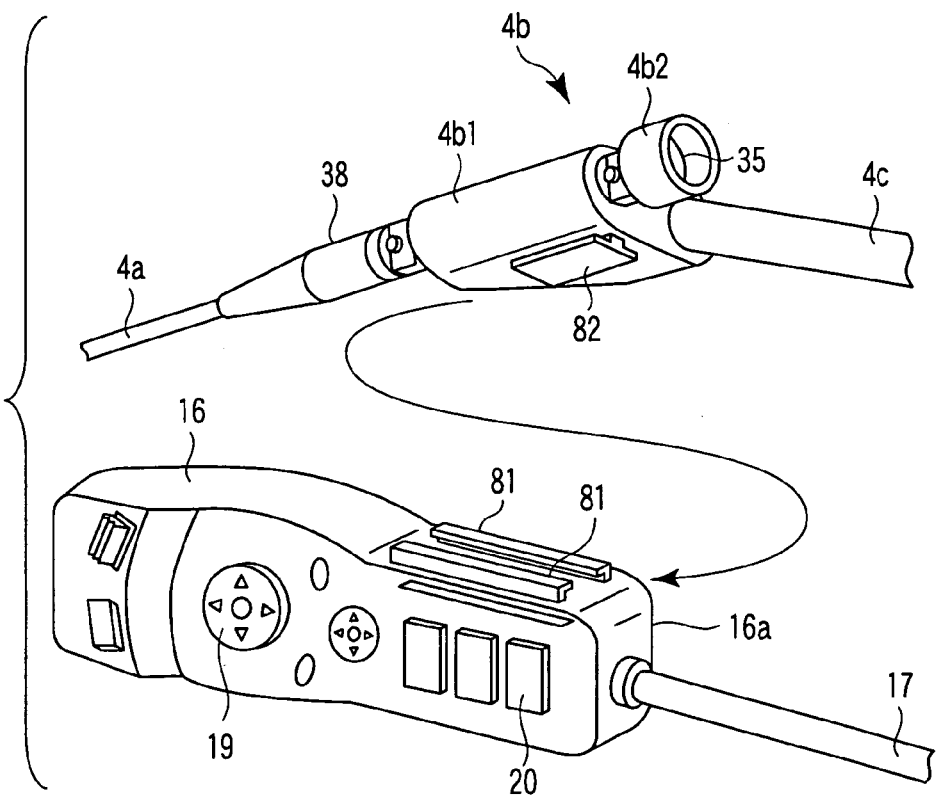
FIG. 23 is a perspective view showing a configuration of essential portions in an endoscope apparatus for industrial use according to a fifth embodiment of the present invention.

FIG. 23 shows a configuration of essential portions of an endoscope apparatus 1 for industrial use according to a fifth embodiment of the present invention. In the present embodiment, a configuration of the linking portion between the intermediate linking portion 4b of the scope portion 4 and the remote controller 16 has been changed as follows.

In the present embodiment, a pair of left and right attaching guide rails 81 are provided along the longitudinal direction of the main body 16a at one side part of the main body 16a of the remote controller 16.

A T-shaped attaching member 82 to be inserted and attached by sliding between the guide rails 81 is formed at the grip portion 4b1 of the scope portion 4. The T-shaped attaching member 82 is inserted into the guide rail 81, whereby the intermediate linking portion 4b of the scope portion 4 and the remote controller 16 are linked with each other. In addition, the t-shaped attaching member 82 is pulled out from the guide rail 81, whereby the remote controller 16 and scope portion 4 can be separated, and can be used independently. There may be provided a stopper function for preventing the T-shaped attaching member 82 from unexpectedly slip off from the guide rail 81.

In the present embodiment as well, the opening direction of the forceps 35 opening when the scope portion 4 and the remote controller 16 are linked with each other is oriented to the side of the cable 17. An operation of the joystick 19 by the left hand and an operation of the manipulating device 43 by the right hand do not interfere with each other, so that these operations can be carried out respectively. In this manner, in the present embodiment as well, there is an advantageous effect that the usability of the endoscope apparatus 1 for industrial use can be improved.

Figure 24A:
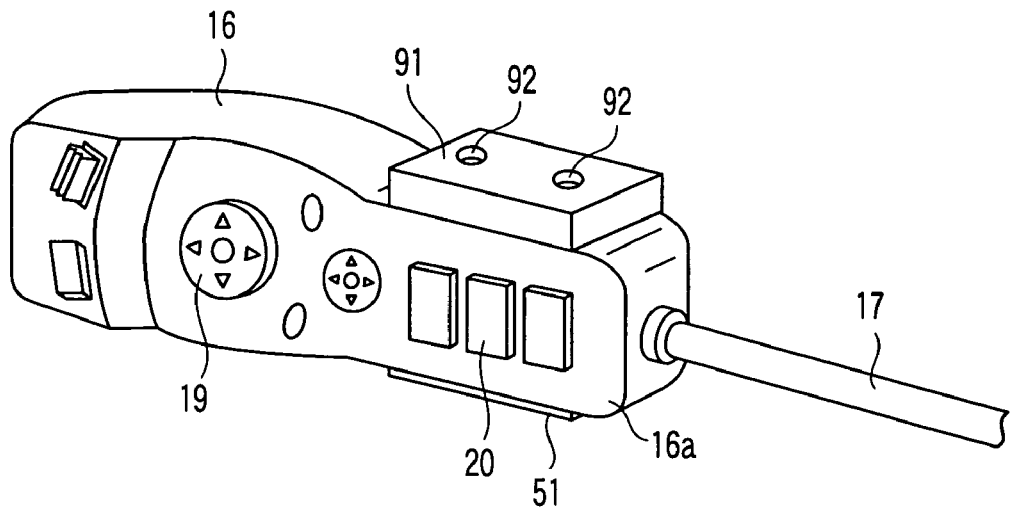
FIG. 24A is a perspective view showing a state a linking member is mounted on a remote controller of an endoscope apparatus for industrial use according to a sixth embodiment of the present invention.
Figure 24B:
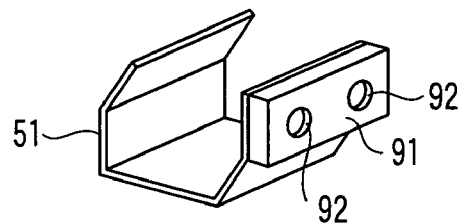
FIG. 24B is a perspective view showing the linking member.
Figure 24C:
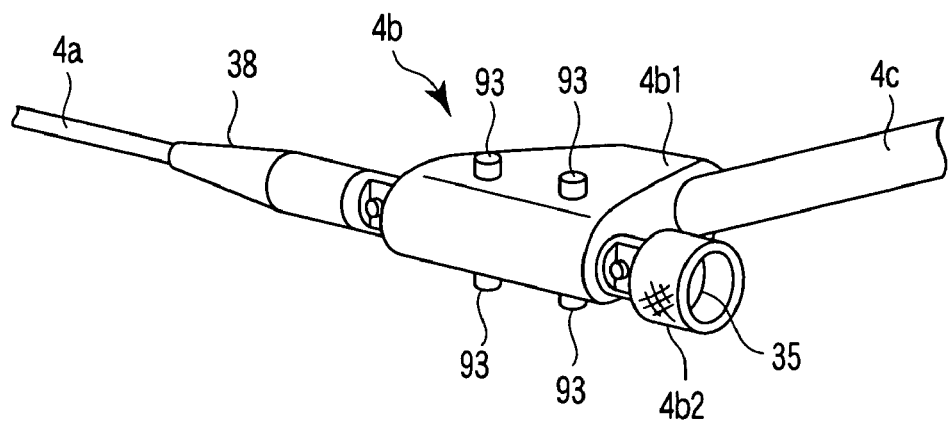
FIG. 24C is a perspective view showing a linking portion between a proximal end part of an insert portion and a universal cable.

FIGS. 24A to 24C each show a configuration of essential portions of an endoscope apparatus 1 for industrial use according to a sixth embodiment of the present invention. In the present embodiment, a configuration of the linking portion between the intermediate linking portion 4b of the scope portion 4 and the remote controller 16 in the endoscope apparatus 1 for industrial use according to the second embodiment described previously (refer to FIGS. 18 to 20A and 20B) has been changed as follows.

In the present embodiment, as shown in FIG. 24B, a flat-plate-shaped N pole of a permanent magnet 91 is fixed to one side part of the flat-plate-shaped connecting device 51. Two engaging holes 92 are formed on a main face of the permanent magnet 91. This connecting device 51 is mounted on the main body 16a of the remote controller 16 as shown in FIG. 24A. During this mounting, the main face of the permanent magnet 91 is disposed outwardly on a side face of the remote controller 16.

As shown in FIG. 24C, at the grip portion 4b1 of the scope portion 4, two engaging protrusions 93 corresponding to the two engaging holes 92 of the permanent magnet 91 are provided respectively on both sides. These engaging protrusions 93 are formed by a S pole of permanent magnet.

The engaging hole 92 of the magnet 91 of the connecting device 51 is attached with the engaging protrusion 93 of the grip portion 4b1, whereby they are magnetically attracted and bonded with each other, and the intermediate linking portion 4b of the scope portion 4 and the remote controller 16 are linked with each other. This linking is due to the permanent magnet, and the removal is easily and universally carried out.

Also in the present embodiment, the opening direction of the forceps opening 35 when the scope portion 4 and the remote controller 16 are linked with each other is oriented to the side of the cable 17. An operation of the joystick 19 by the left hand and an operation of the manipulating device 43 by the right hand do not interfere with each other, and thus, these operations can be easily carried out, respectively.

In the present embodiment as well, when there is no need to use the manipulating device 43 such as a forceps, the intermediate linking portion 4b is pulled out in advance from the connecting device 51 of the remote controller 16, and the remote controller 16 and the intermediate linking portion 4b of the scope portion 4 can be used to be separated from each other. In this manner, in the present embodiment as well, there is an advantageous effect that the usability of the endoscope apparatus 1 for industrial use can be improved.

Figure 25A:
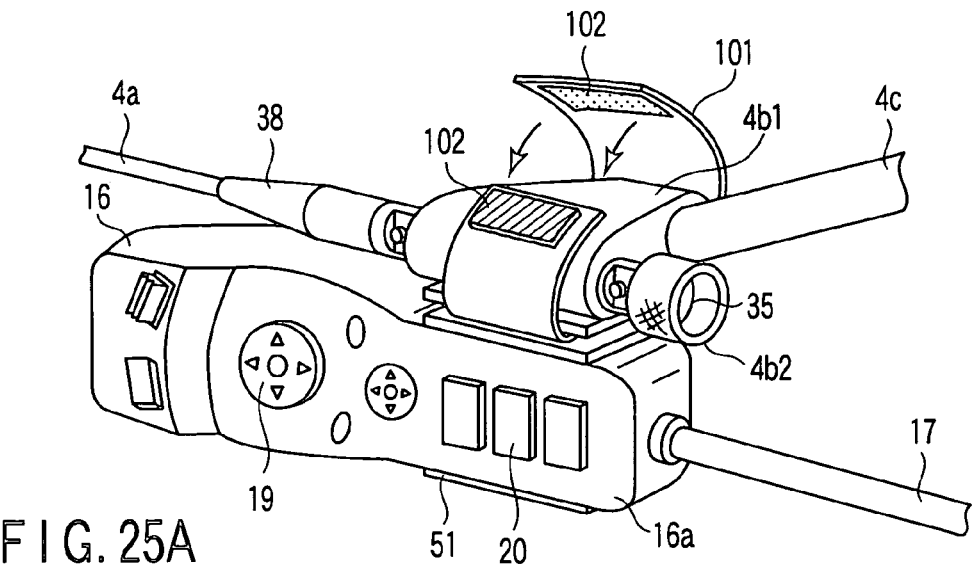
FIG. 25A is an illustrative view for illustrating a work of linking a linking portion between a proximal end part of an insert portion and a universal cable by means of a linking member of an endoscope apparatus for industrial use according to a seventh embodiment of the present invention.
Figure 25B:
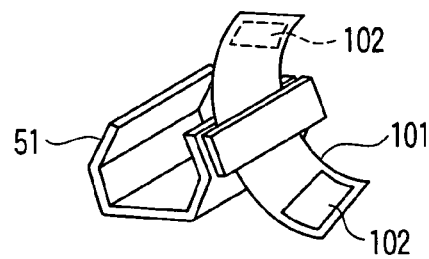
FIG. 25B is a perspective view showing the linking member.

FIGS. 25A and 25B each show a seventh embodiment of the present invention.

In the present embodiment, a configuration of the linking portion between the intermediate linking portion 4b of the scope portion 4 and the remote controller 16 in the endoscope apparatus 1 for industrial use according to the sixth embodiment (refer to FIGS. 24A to 24C) has been changed as follows.

In the present embodiment, as shown in FIG. 25B, a fixing belt 101 is provided at one side part of the plate-spring-shaped connecting device 51 instead of the magnet 91 according to the sixth embodiment. Surface fasteners 102 such as a Velcro tape (registered trademark), for example, are provided at both ends of this fixing belt 101.

With this configuration, when the intermediate linking portion 4b of the scope portion 4 and the remote controller 16 are linked with each other, the connecting device 51 is mounted in advance on the main body 16a of the remote controller 16 as shown in FIG. 25A. Then, the fixing belt 101 of the connecting device 51 is fixed to be wound around the grip portion 4b1 in a state in which the grip portion 4b1 of the intermediate linking portion 4b of the scope portion 4 is disposed at the side part of the remote controller 16. Therefore, by means of the fixing belt 101, the intermediate linking portion 4b of the scope portion 4 and the remote controller 16 are linked with each other.

In the present embodiment as well, the opening direction of the forceps 35 when the scope portion 4 and the remote controller 16 are linked with each other is oriented to the side of the cable 17. An operation of the joystick 19 by the left hand and an operation of the manipulating device 43 by the right hand do not interfere with each other, and thus, these operations can be easily carried out, respectively.

Also the present embodiment, when there is no need to use the manipulating device 43 such as a forceps, surface fasteners 102 of the fixing belt 110 of the connecting device 51 of the remote controller 16 are pulled away from each other in advance, the bondage of the intermediate linking portion 4b of the scope portion 4 by the fixing belt 101 can be released. In this manner, there is an advantageous effect that the remote controller 16 and the intermediate linking portion 4b of the scope portion 4 can be used to be separated from each other, and the usability can be improved.

Figure 26:
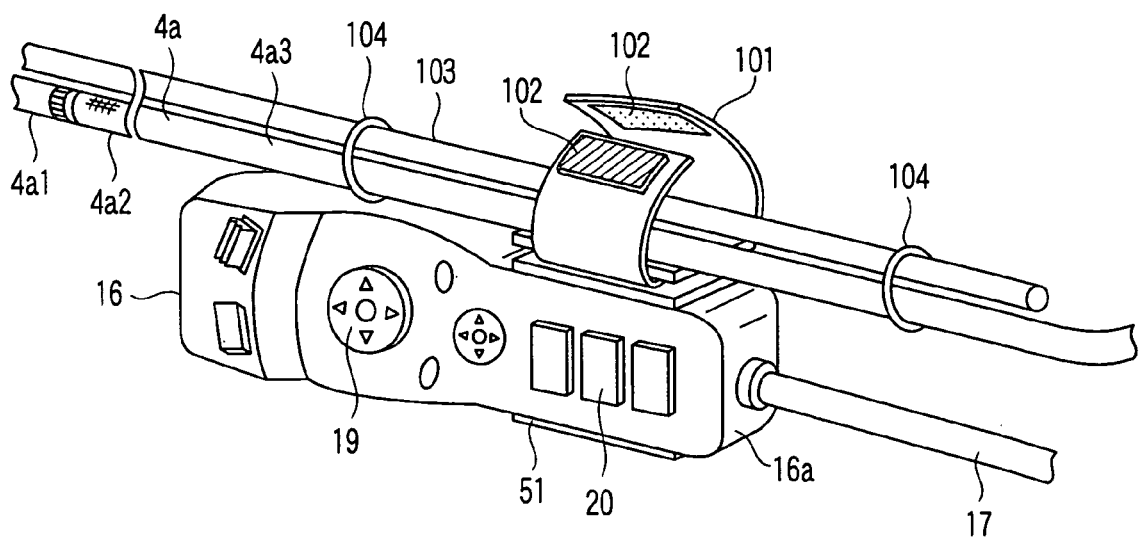
FIG. 26 is a perspective view showing a configuration of essential parts in an endoscope apparatus for industrial use according to an eighth embodiment of the present invention.
Figure 27A:
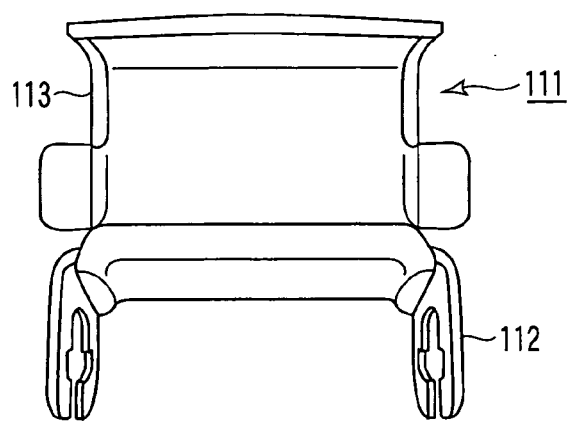
FIG. 27A is a perspective view showing a ninth embodiment of the present invention and showing a linking member mounted on a remote controller.
Figure 27B:
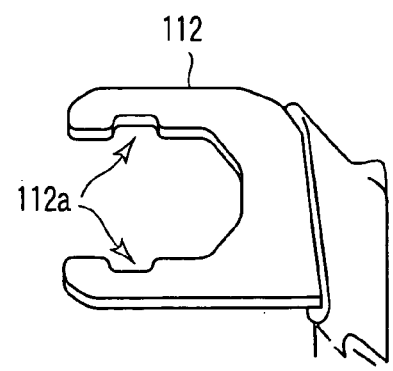
FIG. 27B is a view showing an attaching portion of the linking member.
Figure 27C:
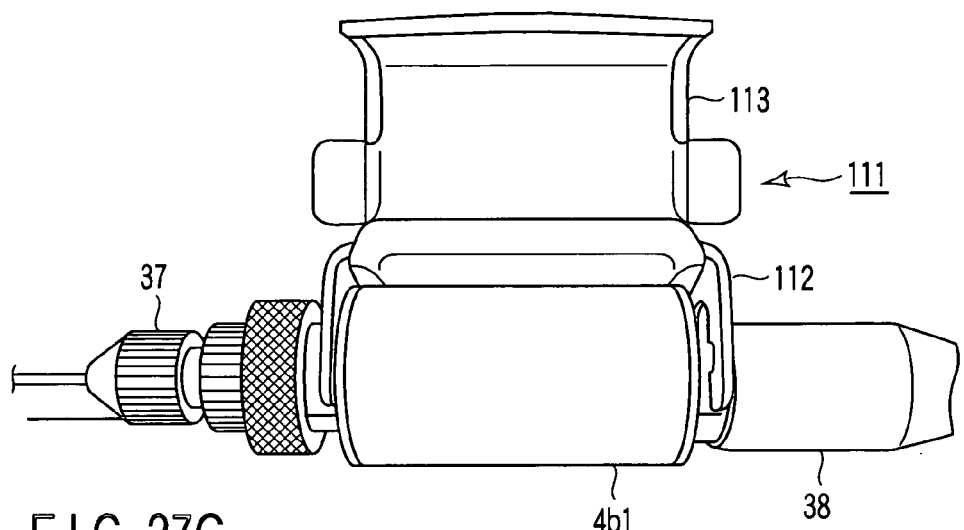
FIG. 27C is a perspective view showing a linking portion between a proximal end part of an insert portion and a universal cable.
Figure 27D:
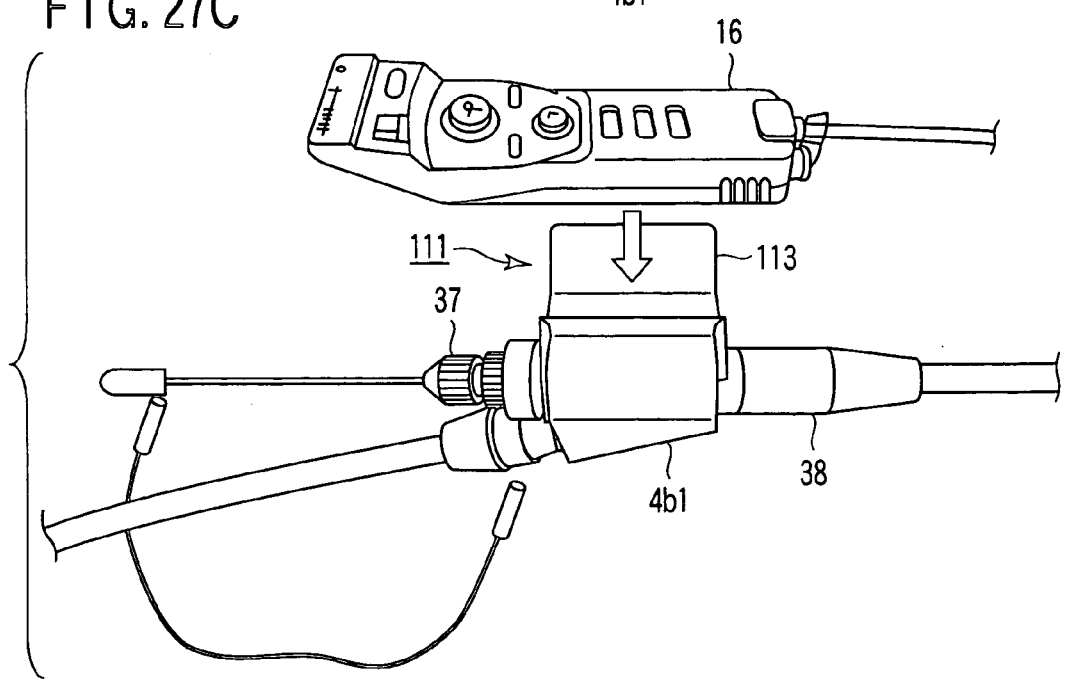
FIG. 27D is a perspective view showing a state in which the remote control of the endoscope apparatus for industrial use is mounted on the linking member.

FIG. 26 shows an eighth embodiment of the present invention.

In the present embodiment, an external channel 103 is provided at the scope portion 4 in the endoscope apparatus 1 for industrial use according to the seventh embodiment described previously (refer to FIGS. 25A and 25B).

This external channel 103 is bonded by a plurality of bonding devices 104 together with the scope portion 4, and is integrated with each other. Then, the scope portion 4 with the external channel 103 and the remote controller 16 are linked with each other by means of the fixing belt 101 of the connecting device 51 of the remote controller 16 shown in the seventh embodiment in a state in which the scope portion 4 with the external channel 103 is disposed at the side part of the remote controller 16.

In the present embodiment, the scope portion 4 with the external channel 103 can be used to be linked with the remote controller 16 as required. In addition, in the present embodiment as well, when there is no need to use the manipulating device 43 such as a forceps, the surface fasteners 102 of the fixing belt 101 of the connecting device 51 of the remote controller 16 are pulled away from each other, whereby the bondage of the scope portion 4 with the external channel 103 by the fixing belt 101 is released from each other in advance.

In this manner, the remote controller 16 and the scope portion 4 with the external channel 103 can be used to be separated from each other. Therefore, also in the present embodiment, there is an advantageous effect that the usability of the endoscope apparatus 1 for industrial use can be improved.

FIGS. 27A to 27D each show a configuration of a linking portion for integrally holding a grip portion of a scope portion and a remote controller in an endoscope apparatus for industrial use according to a ninth embodiment of the present invention. In essential constituent elements of the present embodiment, like constituent elements in the first embodiment described previously are designated by like reference numerals, so a duplicate description of these elements is omitted here.

In the present embodiment, there is provided a connecting device 111 for integrally and detachably holding the intermediate linking portion 4b of the scope portion 4 and the remote controller 16. In this connecting device 111, as shown in FIGS. 28A and 28B, a substantially U-shaped opening for detachably attaching the intermediate linking portion 4b is provided. At both sides, the connecting device is composed of: an attaching portion 112 having provided thereat a cutout portion which serves as a stopper portion 112a; and a remote controller mount portion 113 capable of mounting and holding the remote controller 16. This attaching portion 112 is configured in the same manner as the attaching portion 51a (51b) described previously.

This connecting device 111 is attached as shown in FIG. 28B in a state in which the attaching portion 112 is mounted to be inserted into both end sides of the grip portion 4b1 of the intermediately linking portion 4b. Further, the remote controller 16 is mounted on the remote controller mount portion 113, and is held integrally with the grip portion 4b1. The connecting device 111 shown in FIG. 28A can be mounted on the channel port section 4b2 irrespective of the front or back of the attaching portion 112 relevant to the grip portion 4b1. Thus, this connecting device can be mounted on either of the left and right of the channel port section 4b2.

Figure 28:
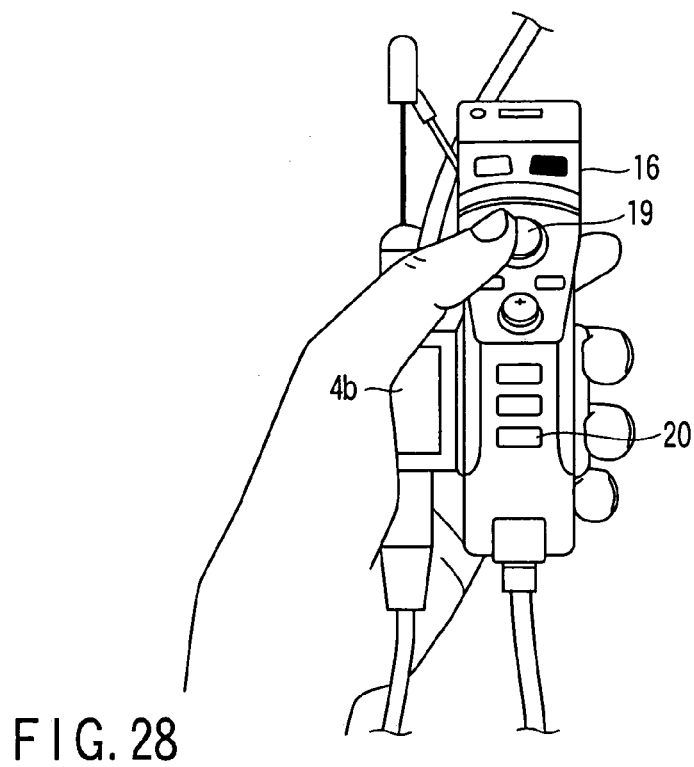
FIG. 28 is a view showing an operating state of the remote controller in an endoscope apparatus for industrial use according to the ninth embodiment.

In this holding state, as compared with the holding state shown in FIG. 18, the grip portion 4b1 is mounted on the opposite side of the remote controller 16, and the upward site (forceps 35) of the remote controller 16 is mounted at the side of the fixing bracket 37. Therefore, as shown in FIG. 28, the joystick 19 is operated by the thumb of the left hand while the remote controller 16 is gripped by the left hand.

Figure 29:
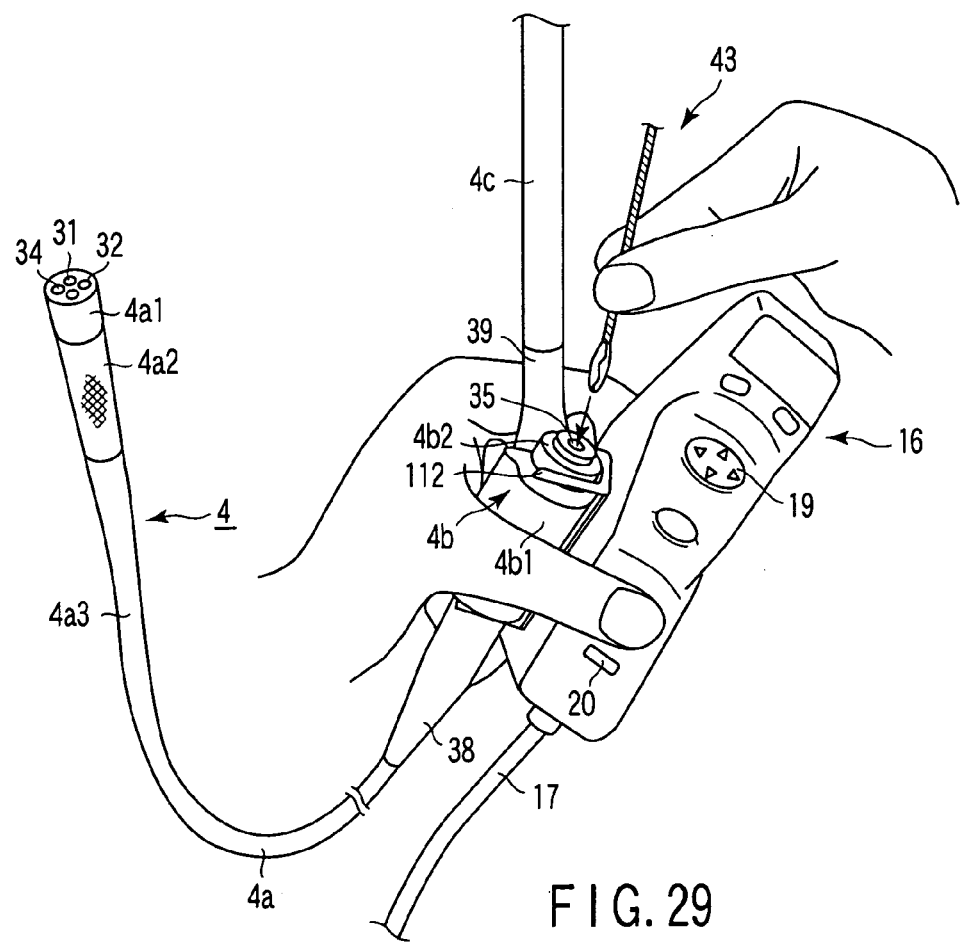
FIG. 29 is a perspective view showing a state in which a forceps is inserted into a forceps opening of a grip portion in the endoscope apparatus for industrial use according to the ninth embodiment.

As shown in FIG. 29, in the case of using the manipulating device such as a forceps, while the remote controller 16 is held by the fingertip so as to envelope the grip portion 4b1 by the palm of the left hand, the manipulating device 43 is held by the right hand, and is inserted into the forceps opening 35 of the channel port section 4b2 from the frontal side.

Therefore, the grip portion 4b1 is kept stable because it is held by the palm, and the work of inserting the manipulating device 43 can be easily carried out.

Next, a tenth embodiment of the present invention will be described.

Figure 30A:
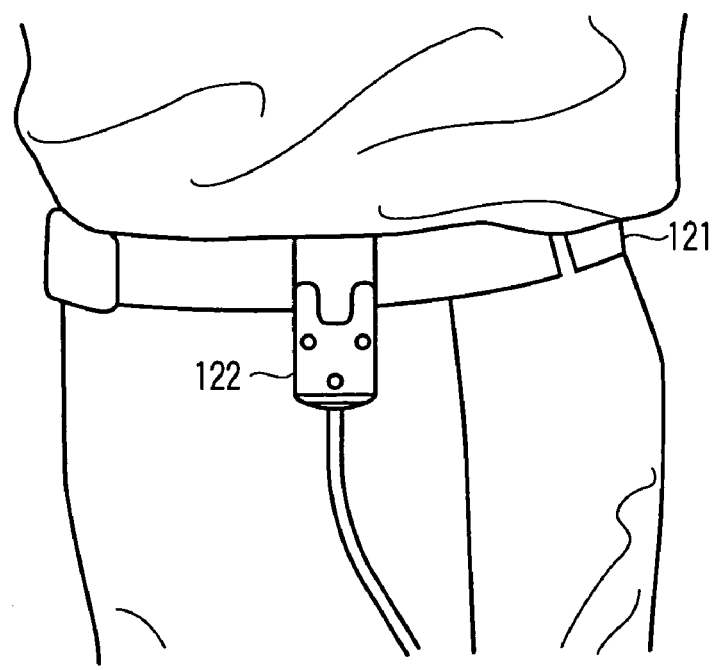
FIG. 30A is a view showing a state in which a belt clamp is mounted on a body according to a tenth embodiment of the present invention.
Figure 30B:
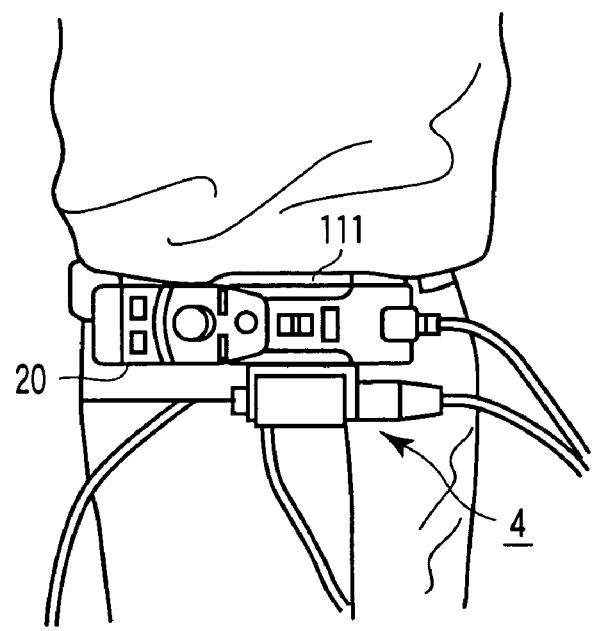
FIG. 30B is a view showing a state in which a connecting device is mounted on the belt clamp.

FIG. 30A is a view showing a state in which a belt clamp is mounted on a body. FIG. 30B is a view showing a state in which a connecting device is mounted on the belt clamp.

The connecting device 111 according to the ninth embodiment described previously can be mounted as shown in FIG. 30B on a belt clamp 122 mounted on an operator's belt (trouser) 121 shown in FIG. 30A.

According to such an embodiment, in the case of movement or carrying out other work, both hands are free, and everything is carried to a movement place together with the operator, which is very convenient. In addition, even in the case where other work is carried out on the spot, nothing needs to be placed on a floor or the like. Thus, there is no danger that the operator drops something carelessly or steps on something.

Next, an eleventh embodiment of the present invention will be described.

Figure 31:
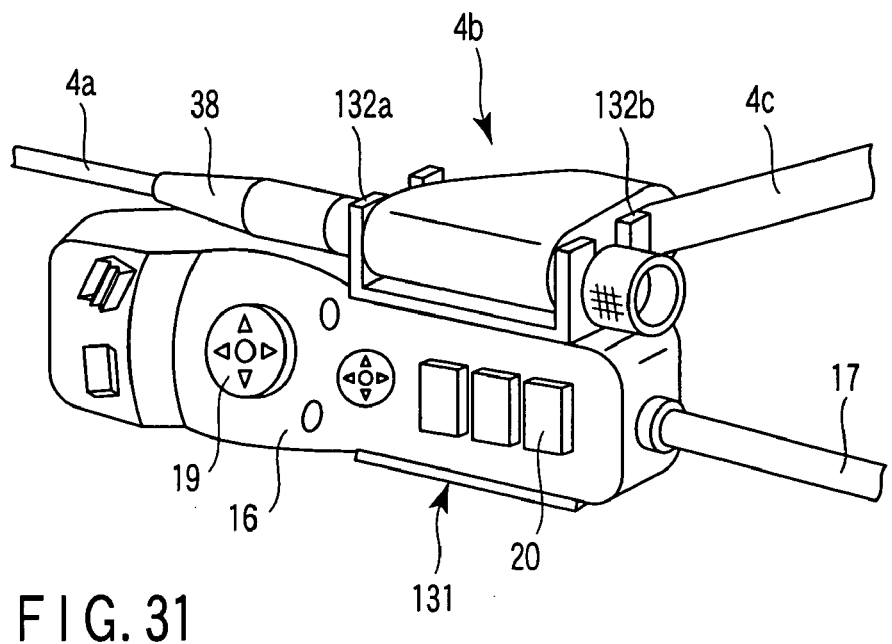
FIG. 31 is a perspective view showing a state in which a grip portion is linked with a remote controller of an endoscope apparatus for industrial use according to an eleventh embodiment via a connecting grip.

FIG. 31 shows a configuration of a connecting portion for integrally holding a grip portion of a scope portion and a remote controller in an endoscope apparatus for industrial use according to an eleventh embodiment. A connection device 131 according to the present embodiment detachably links the remote controller 16 and the intermediate linking portion 4b of the scope portion 4, and a belt clip (a belt clip 136 shown in FIG. 32B) which can be mounted on a belt 15 is provided.

Figure 32B:
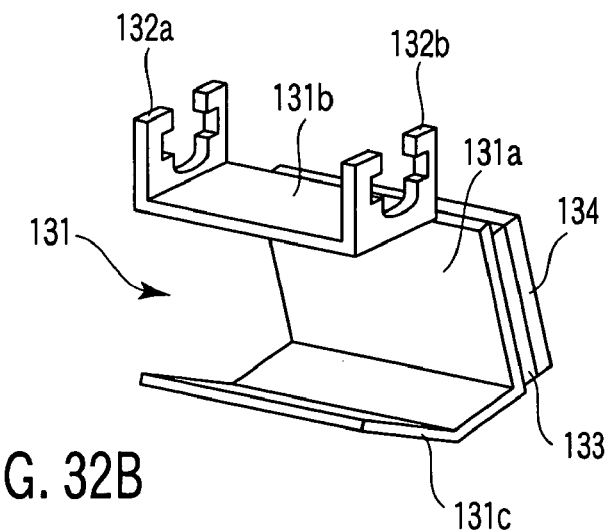
FIG. 32B is a perspective view showing the connecting grip.
Figure 32A:
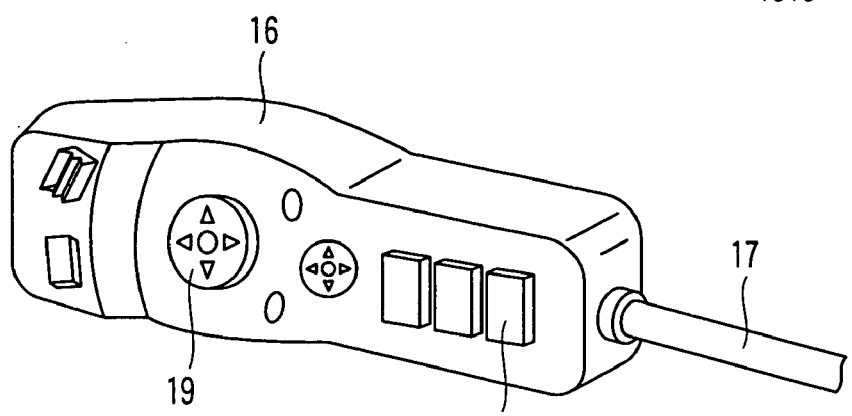
FIG. 32A is a perspective view showing a state in which the connecting grip is removed from the remote controller of the endoscope apparatus for industrial use according to the eleventh embodiment.
Figure 33:
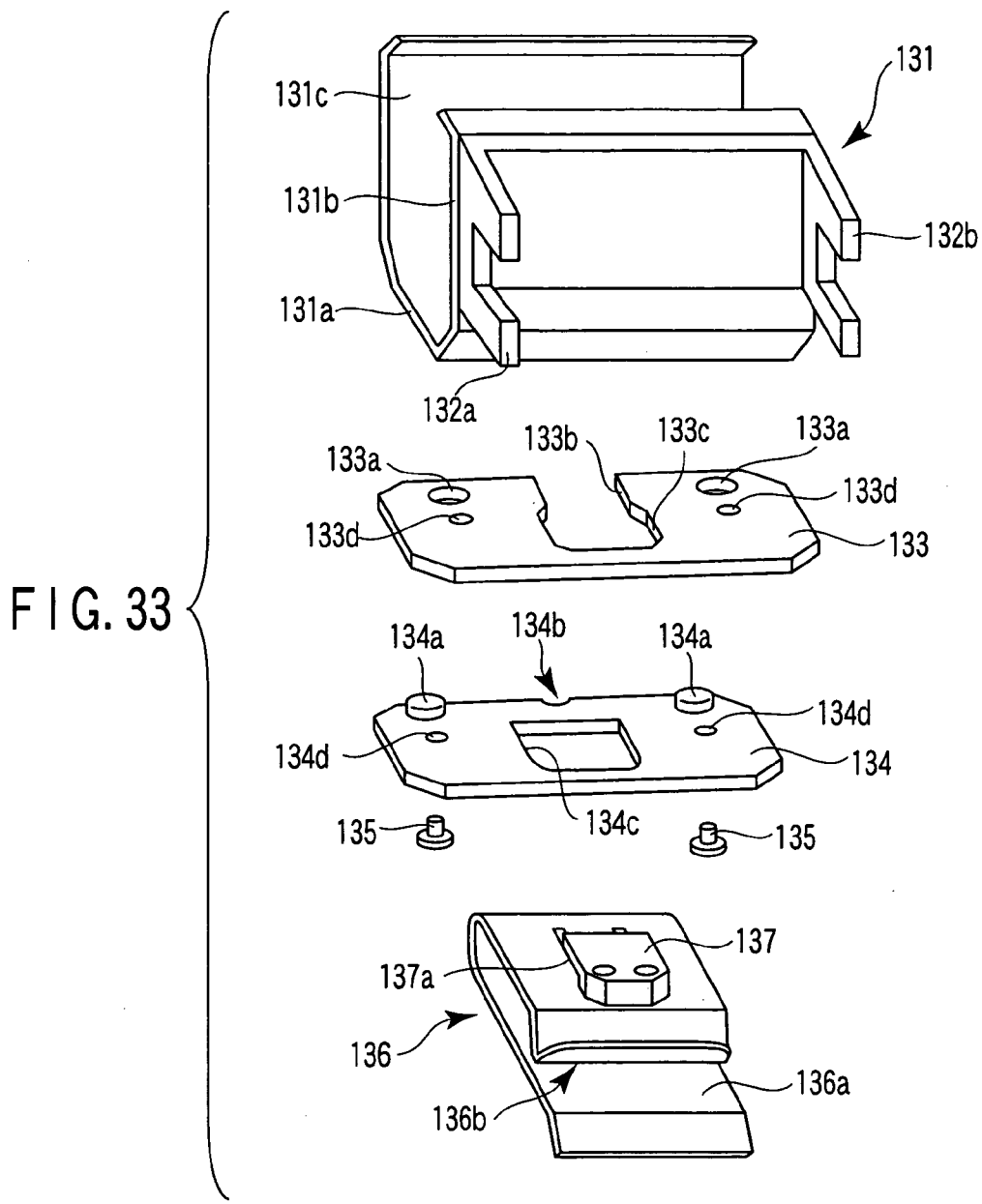
FIG. 33 is an exploded perspective view showing the connecting grip of the endoscope apparatus for industrial use according to the eleventh embodiment.

FIG. 32B shows a configuration of this connecting device 131.

Figure 34:
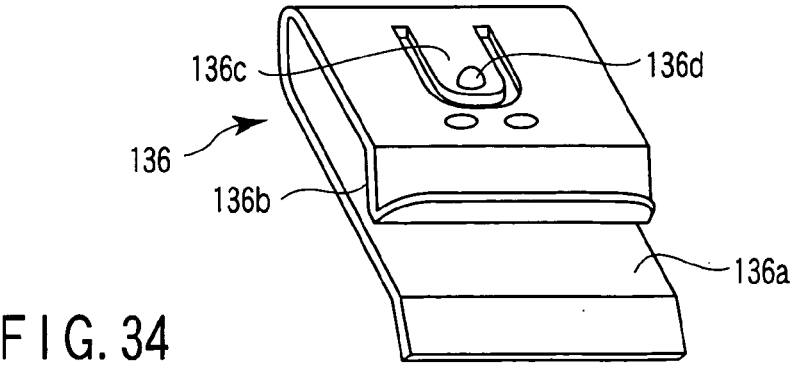
FIG. 34 is a perspective view showing a belt clip of the endoscope apparatus according to the eleventh embodiment.

In this connecting device 131, arm portions 131b and 131c for elastically gripping the remote controller 16 are provided respectively at both ends of the top and bottom of a substantially flat-plate shaped base face 131a. As shown in FIG. 31, a gap between the arm portions 131a and 131c is set in dimensions such that these arm portions come into contact with a side face of the remote controller 16. Attaching portions 132a and 132b are provided at one side of the arm portion 131b. The intermediate linking portion 4b is removable from the attaching portions 132a and 132b. Further, the base face 131a of the connecting device 131 is removable from the belt clip 136 (FIG. 34).

A description of the connecting device 131 will be given with reference to FIGS. 32A, 32B, 33, and 34.

This connecting device 131 is integrally configured by a rivet 135 when an engaging base 134 and a rotation stop base 133 are laminated.

At the engaging base 134, there are provided: two protrusions 134a, a cutout 134b, a first opening 134c to be attached with a play to a stator 137 (described later); and two first through holes 134d.

At the rotation stop base 133, there are provided: a mounting hole 133a to be attached with a protrusion 134a; a rotation stop cutout 133b to be attached with a side face of a stator 137; a second opening 13c to be attached, with a certain play, to the stator 137; and a second through hole 133d whose position is aligned with the first through hole 134d. The rivet 135 is routed through the second through hole 133d and the first through hole 134d, and further, is routed through a through hole (not shown) provided at the connection device 131 to be riveted.

The cutout 134b of the above engaging base 134; the first opening 134c; the rotation stop cutout 133b of the rotation stop base 133; and the second opening 133c are aligned with each other on a central axis. The second opening 133c and the first opening 134c are equal to each other in width.

In the belt clip 136, a clip main body 136a and the stator 137 are riveted.

As shown in FIG. 34, the clip main body 136a includes a pinch portion 136b, a plate spring portion 136c, and a click protrusion 136d. The stator 137 is mounted so as to cover the click protrusion 136d. The stator 137 has a lateral width attached with the rotation stop cutout 133b, and has a stepped portion 137a on a side facing the clip main body 136a. The stepped quantity of the stepped portion 137a is as large as a thickness such that the plate thickness of the engaging base 134 can be housed in a slight gap.

Now, an operation of the thus configured connecting device 131 will be described below. A link between the connecting device 131 and the belt clip 136 in this endoscope apparatus 1 is carried out as follows.

Figures 35A, 35B:
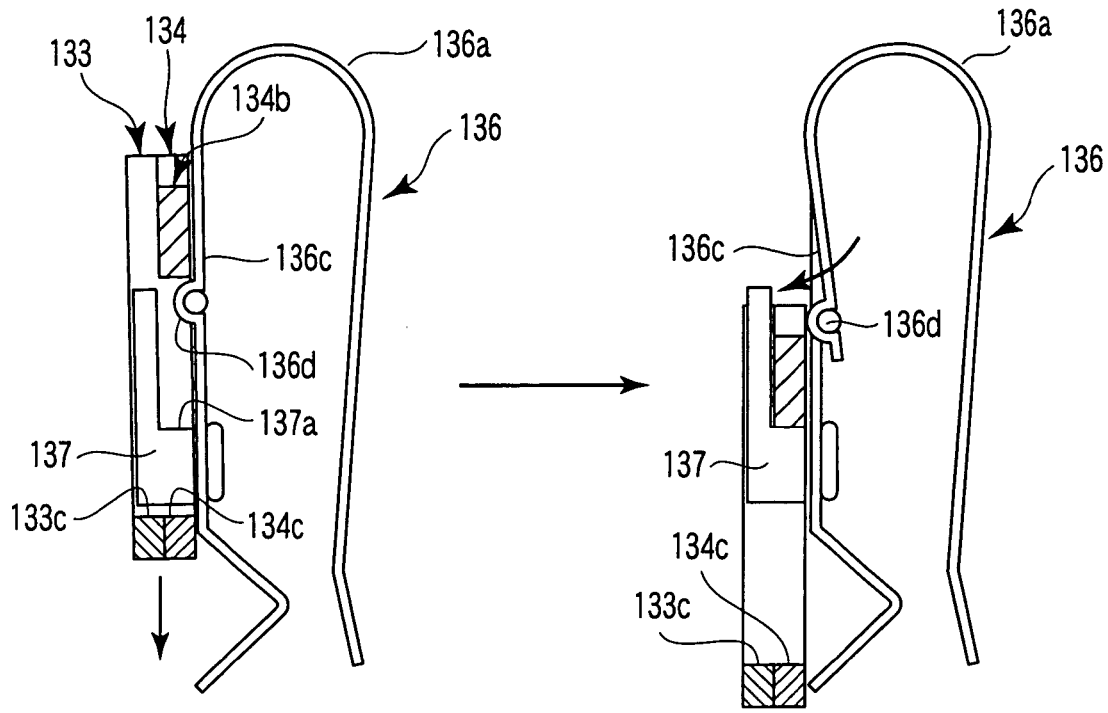
FIG. 35A is a longitudinal cross section showing a state in which a stator is attached with a play to a first opening and a second opening of the belt clip of the endoscope apparatus according to the eleventh embodiment.
FIG. 35B is a longitudinal cross section showing a state in which the connecting grip is moved in a downward direction.

FIG. 35A shows a state in which the stator 137 is attached with a play to the first opening 134c of the engaging base 134 and the second opening 133c of the rotation stop base 133.

In this state, when the connecting device 131 is moved in a direction indicated by the downward arrow in FIG. 35A, the state shown in FIG. 35B is obtained. At this time, the stepped portion 137a pinches the engaging base 134. In addition, a surface of the engaging base 134 is pushed upwardly on the click protrusion 136d, and is slackened by the plate thickness 134c of the engaging base 134. As a result, a biasing force is generated.

Then, when the click protrusion 136d reaches a position of one arm portion 131b, the click protrusion 136d is indented at one arm portion 131*b* by the biasing force, and the mounting is completed. In addition, this indention is transmitted to an operator as the feeling of completed mounting.

By means of such mounting, the connecting device 131 does not slip off from the belt clip 136 unexpectedly. In addition, since the stator 137 and the rotation stop cutout 133*b* are in close contact with each other, a mount state free of undesired play is obtained. In the case of removal, operation is carried out by reversing the mounting procedures described previously. Further, when the arm portion 131*b* and the click protrusion 136*d* are removed from each other, one can feel a slight click, and can recognize that the removal is completed.

Figure 36:
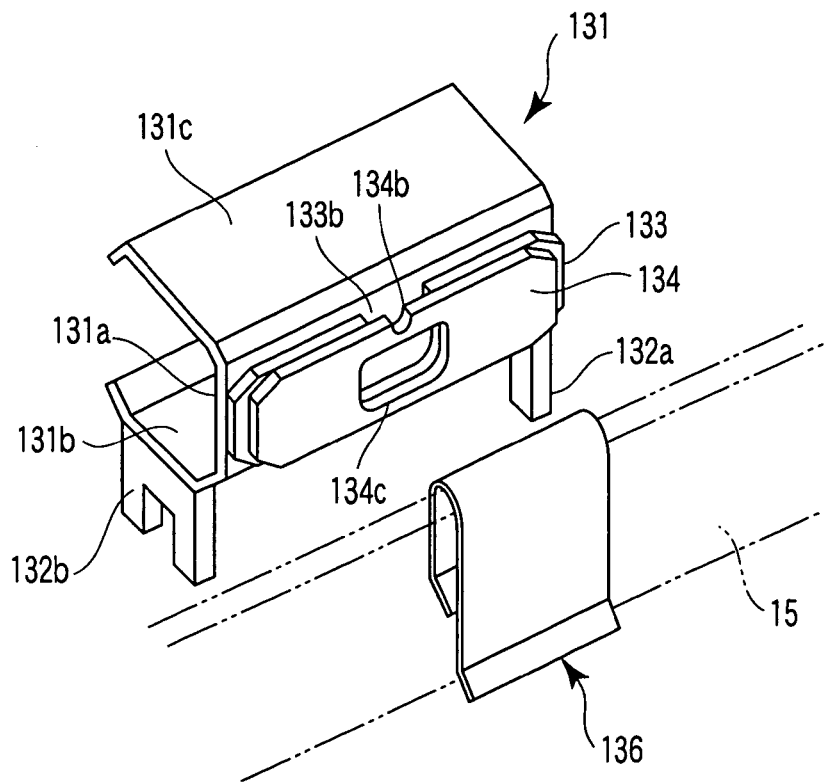
FIG. 36 is a perspective view showing a state in which the connecting grip is rendered to approach the belt clip mounted on an operator's belt in the endoscope apparatus for industrial use according to the eleventh embodiment.

FIG. 36 shows a state in which the mounting of the connecting device 131 is approached with respect to the belt clip 136 mounted on a belt 130 of an operator H. This belt clip 136 is not limited to the belt 130 in mounting portion, and may be mounted at another portion such as another device, another mounting device of the operator H, for example, the operator's uniform pocket.

With such a configuration, the connecting device according to the present embodiment can be easily mounted on and removed from an operator or a device in the vicinity of the operator in a state in which the grip portion 4*b* of the scope portion 4 and the remote controller 16 are linked integrally with each other. Thus, operation can be carried out efficiently with good workmanship. In addition, in the case of doing other work as well, there is no need to place the scope portion 4 or remote controller 16 on a floor or the like. Thus, damage caused by careless stepping can be prevented. Moreover, since the scope portion 4 and the remote controller 16 are integral, an operation of the remote controller 16 can be carried out while they are held in one hand, and at the same time, a manipulating device can be operated by the other hand. Thus, the work efficiency is improved, so that a burden on an operator is reduced in inspection over a long period of time.

In the case of using the belt clip 136 and connecting device 131 according to the present embodiment, the mounting and removal can be recognized by the feeling of a click, thus enabling reliable mounting and removal without keeping an eye on an object when necessary.

Figure 37:
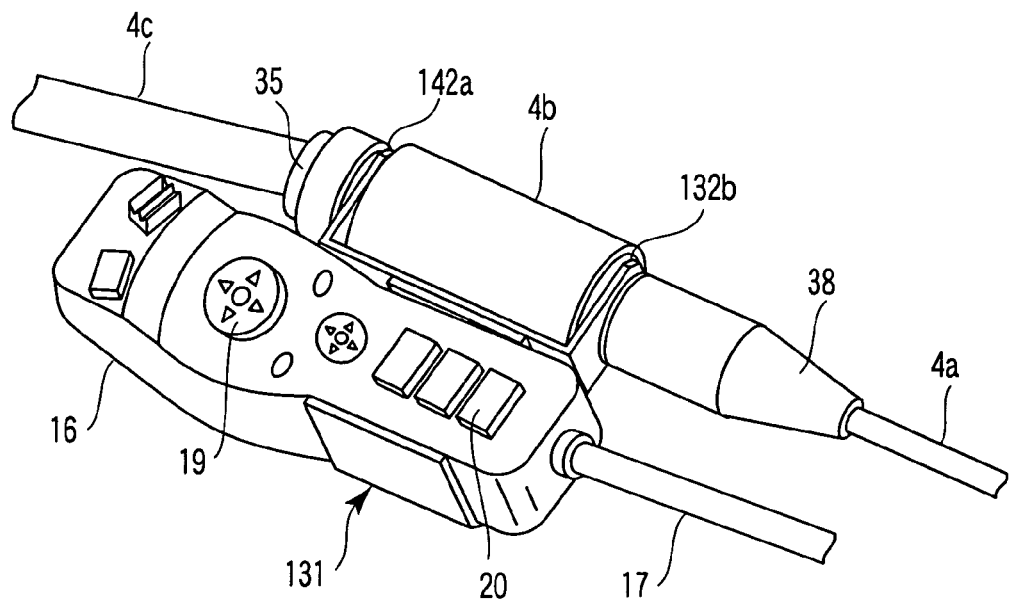
FIG. 37 is a perspective view of essential portions showing a modified example of the endoscope apparatus for industrial use according to the eleventh embodiment.
Figure 38:
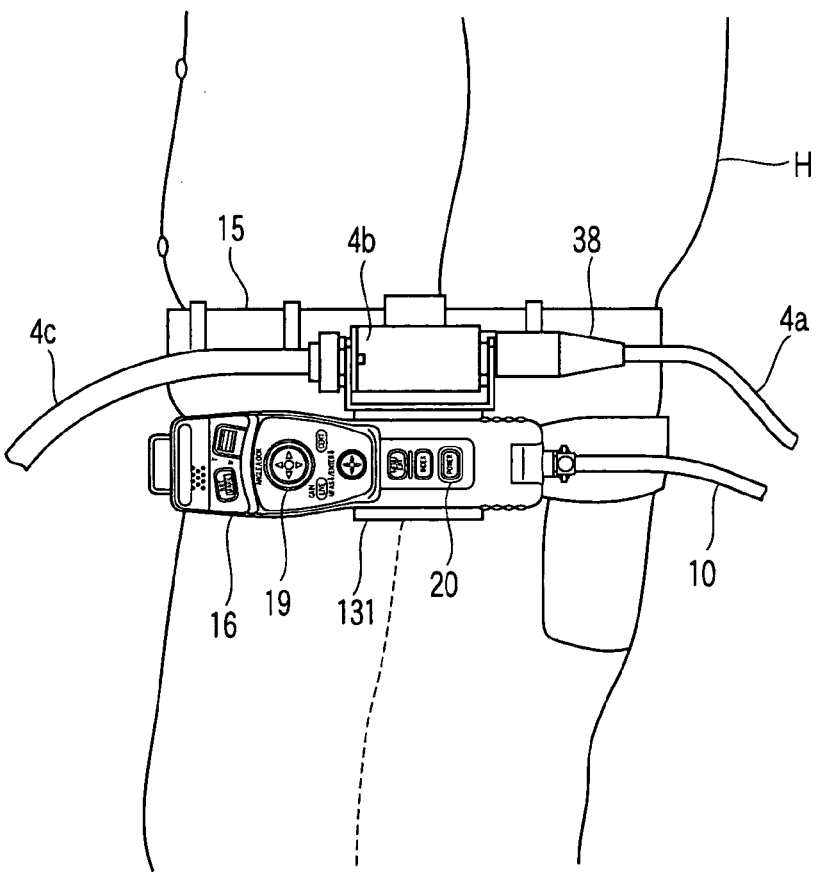
FIG. 38 is a perspective view showing a state in which the connecting grip according to a modified example of the eleventh embodiment is mounted on an operator's belt.
Figures 42A, 42B:
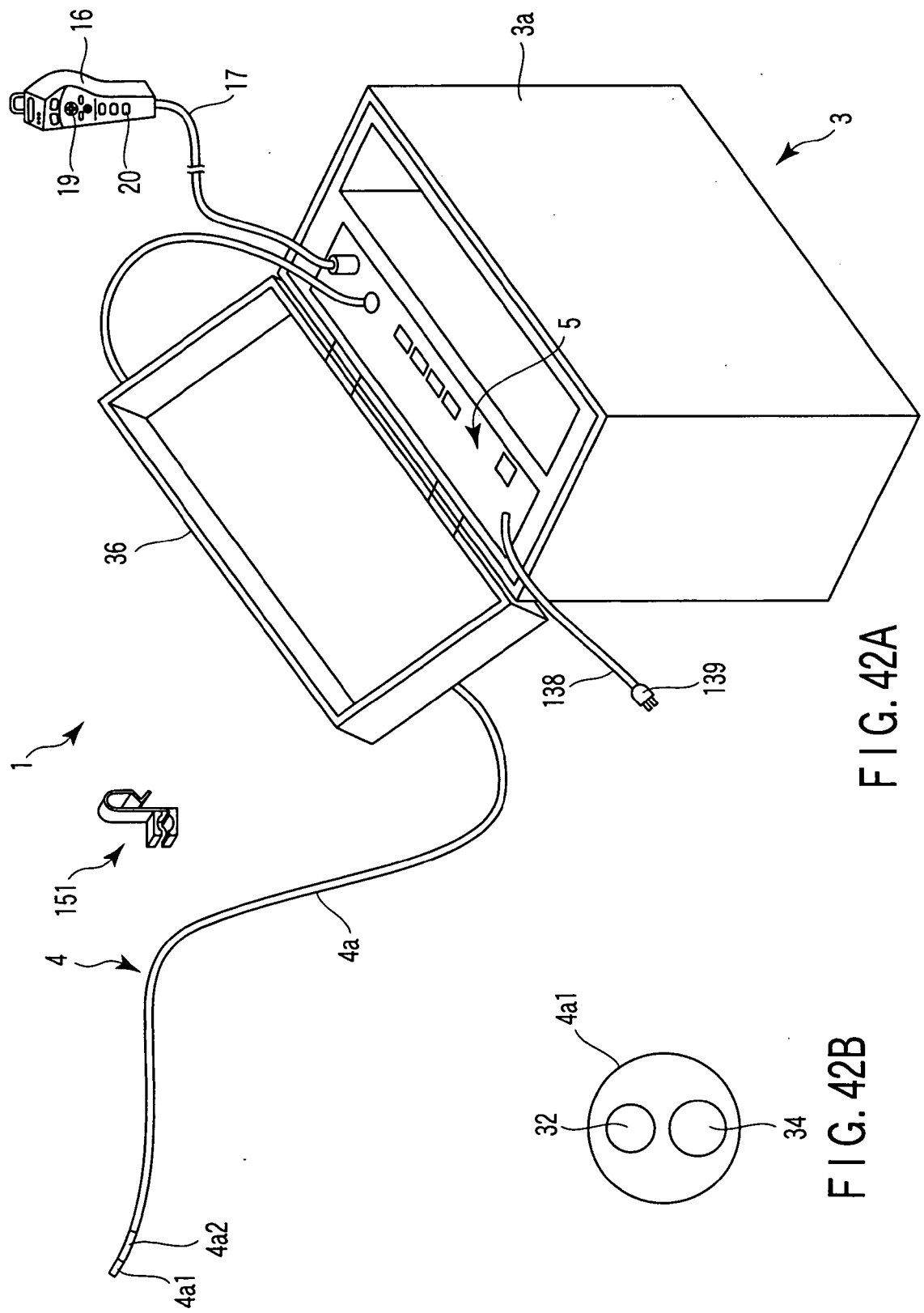
FIG. 42A is a perspective view showing a schematic configuration of an entire endoscope apparatus for industrial use according to a thirteenth embodiment of the present invention.
FIG. 42B is a plan view showing a distal end face of a head portion in the endoscope apparatus for industrial use.
Figure 47:
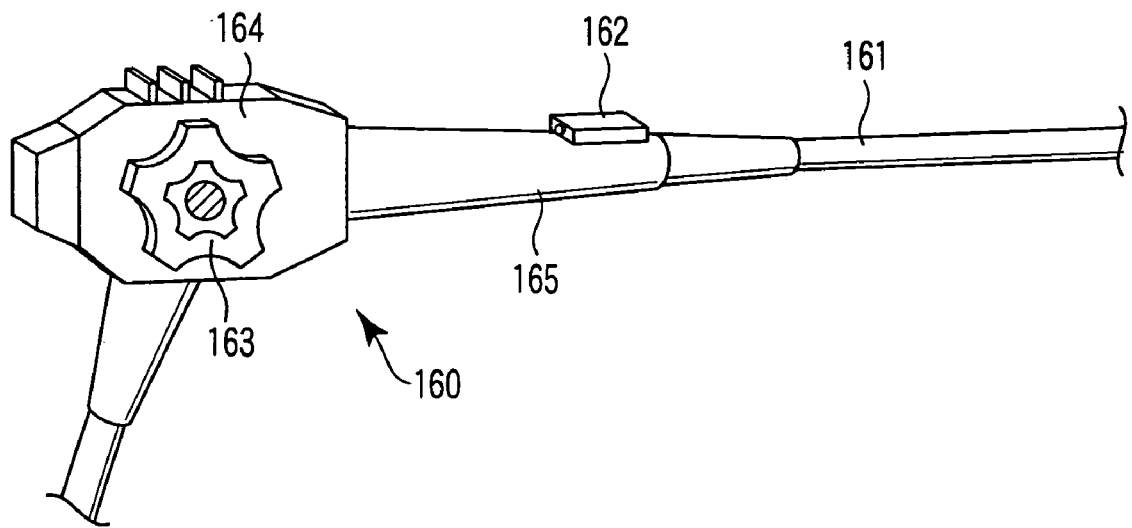
FIG. 47 is a perspective view showing a first example of an operating portion in a conventional endoscope apparatus.
Figure 48:
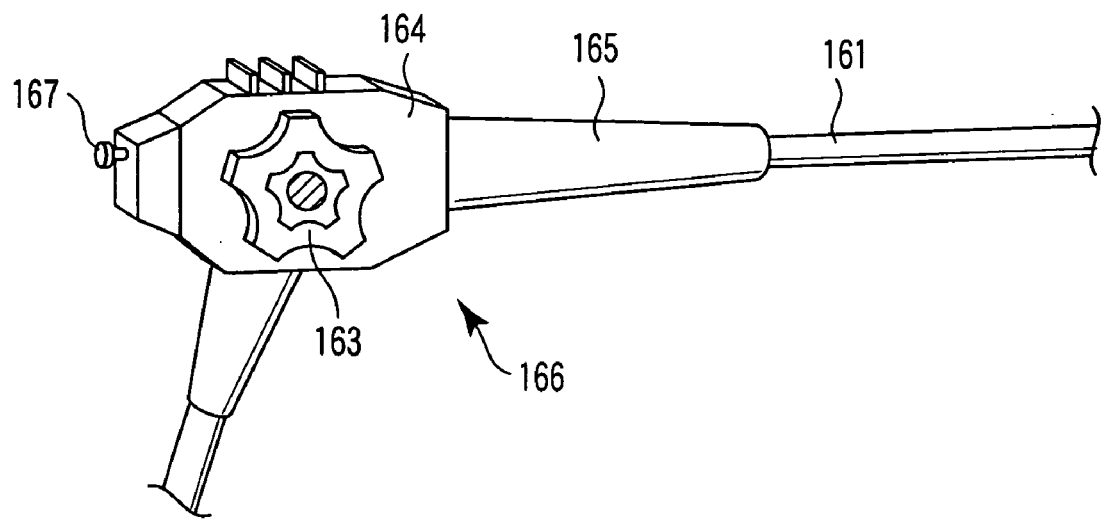
FIG. 48 is a perspective view showing a second example of the operating portion in the conventional endoscope apparatus.

FIGS. 37 and 38 each show a modified example of the endoscope apparatus for industrial use according to the eleventh embodiment described previously.

In this modified example, in a state in which the remote controller 16 and the intermediate linking portion 4*b* of the scope portion 4 are linked with the connecting device 131, the linking direction of the intermediate linking portion 4*b* is reversed with respect to the linking state shown in FIG. 16 according to the eleventh embodiment described previously. When such linking is done, operability is further improved because the channel port section 35 at the rear end part of the intermediate linking portion 4*b* is oriented forwardly of the operator H.

FIGS. 39A, 39B, 40, and 41 each show a twelfth embodiment of the present invention.

In the embodiments each described previously, the remote controller 16 and the scope portion 4 have been provided to be independent of each other. However, in the present embodiment, these elements are integrated with each other. Namely, the present example shows a configuration in which an operating portion 140 having a function identical to the remote controller 16 is mounted on the intermediate linking portion 4*b* of the scope portion 4.

FIG. 40A shows an external configuration of the operating portion 140.

At the operating portion 140, as shown in FIG. 39, there is provided a hand stock portion 141 which a user can grip by a single hand. This hand stock portion 141 mounts: a joystick (flexibly bending operation portion) 142 for remotely operating the flexibly bending portion 4*a*2 of the scope portion 4; and a power button 143. This joystick 142 is a flexibly bending input portion of electrically driven flexibly bending operation type that generates a signal corresponding to a tilt angle by a frontal two-dimensional rod portion operation and flexibly bends the flexibly bending portion 4*a*2 in vertical and horizontal directions.

Further, upward of the hand stock portion 141 of the operating portion 140, there are provided: a monitor portion (display portion) 146 for displaying an image acquired by the scope portion 4; and a forceps opening (proximal opening end) 144 of the internal channel 33. This monitor portion 146 is composed of, for example, a display panel 147 such as a liquid crystal display (LCD); and a frame body 148 for housing this display panel 147. In the internal channel 33, the forceps opening is provided between the monitor portion 146 and the joystick 142. In a casing of the hand stock portion 141, a proximal opening end of the internal channel 33 is linked with the internal end part of the forceps opening 144.

In addition, a universal cable 4C is introduced from the lower end portion of the hand stock portion 141. This universal cable 4C includes: a light guide from the side of the scope portion 4; a signal line for transmission of an image signal outputted from a CCD; and a signal line connected to the display panel 147 of the monitor portion 146.

Belt routing portions 145 are provided at two portions, i.e., at the left and right of the outside face of the hand stock portion 141. By utilizing the belt routing portions 145, as shown in FIG. 41, the operator's belt 130 can be mounted on the operator's body or the like by routing it through these routing portions.

An operation using the thus configured operating portion 140 according to the present embodiment will be described here.

When the endoscope apparatus 1 for industrial use according to the present invention is used, as shown in FIG. 41, the belt 130 is routed through the belt routing portions 145, and the operating portion 140 is mounted on the body of the operator H. The belt 130 may be used by fabricating a dedicated belt other than that worn by the operator H. A belt may be of shoulder type which is specifically fabricated for shoulder suspension, and is not limited to a waist wearing type. The operating portion 140 is thus mounted on the operator's body or the like, whereby both hands are set free, resulting in improved work efficiency and reduction of workload. Therefore, this mounting is efficient for inspection over a long period of time.

FIGS. 42A, 42B, 43, and 44 each show a thirteenth embodiment of the present invention.

In the present embodiment, there is provided a clip portion 151 for mounting the insert portion 4*a* of the scope portion 4 on the body of the operator H.

As shown in FIG. 43, the clip portion 151 is reduced in length at one end side of a plate-shaped base plate 152 bent in a U-shape, and there is provided a plug-in portion 153 at which a V-shaped stopper is formed. A holding portion 154 made of a resin or the like, the holding portion elastically holding an insert portion 4*a* to be pinched, is provided at the other end of the base plate 152.

A U-groove cutout 156 is formed in a three-dimensional shape at this holding portion 154, and a housing portion 155 engraved in a curved face shape is formed such that one side face of the cutout 156 comes into close contact with an external face of the insert portion 4a. The insert portion 4a is pushed to widen the holding portion 154, and is attached in the cutout 156 to be pinched, and is attachably/detachably supported.

In the case where the insert portion 4a of the scope portion 4 is held at the clip portion 151 plugged in the belt 130, a direction parallel to the belt 130 is obtained as shown in FIG. 43.

An operation of the thus configured clip portion 151 according to the present invention will be described here.

When the endoscope apparatus 1 for industrial use according to the present embodiment is used, the operator H mounts the clip portion 151 by plugging it into the belt 130 or the like in advance. The scope portion 4 is held at the clip portion 151 as required.

In the present embodiment, the insert portion 4a can be attached/detached without removing the clip portion 151 from the belt 130, and the operation is easy. Further, a direction in which the clip portion 151 is plugged in the belt 130 is orthogonal to a direction in which the clip portion 151 holds the insert portion 4a. Thus, even if the insert portion 4a is moved or even if the insert portion 4a is mounted or removed, the clip 151 does not slip off from the belt 130. This is because a force line direction in which a force acting when the clip portion 151 is mounted is different from that of a force acting when the insert portion 4a works.

Next, a fourteenth embodiment of the present invention will be described with reference to FIG. 45.

In the present invention, as shown in FIG. 45, there is provided a disk portion 161 which functions as a disk mounted forwardly of the belt 130 of the operator H. An arm member 162 capable of mounting the remote controller 16 is provided on a top face of the disk portion 161. The arm member 162 is formed like a connecting device in the embodiment described previously. The disk portion 161 is formed of a steel material or the like, and a magnet of the remote controller 16 is mounted, whereby attraction and holding due to the magnetic force may be achieved.

With this disk portion 161, an operation manual for equipment to be inspected or the like is placed on a disk face of a top face, contributing to efficient inspection.

Further, FIG. 46 shows a fifteenth embodiment of the present invention.

In the present embodiment, a bag portion 164 is provided at a plate member 163. This bag portion 164 can contain tools, manuals or the like. Therefore, a configuration around the body can be simplified. A holder for holding tools provided may be mounted without being limited to such a bag.

The present invention is not substantially limited to the embodiments each described previously, and various modifications can be made without deviating from the spirit of the invention.

For example, body mount tools (tools to be mounted) include a string, a belt, a cloth, a safety rope (to be worn to ensure safety), a life jacket, a tool pocket and the like. Further, peripheral devices include a jet engine, nuclear power plant, fire power plant, water power plant, chemical plant, food plant, sewage water pipe, boiler, airplane, or other related peripheral apparatus.

According to the present invention, there is provided a connecting portion for detachably connecting either of at least an insert portion and an operating portion to either of at least a wear at the side of an operator's body and a portion to be mounted of a peripheral device. Therefore, operations of the operating portion and the insert portion can be easily carried out, and a burden on gripping the operating portion or insert portion over a long period of time can be reduced. Because of this, there can be provided an endoscope apparatus with good operability capable of easily carrying out the operations of the operating portion and insert portion.

What is claimed is:

1. An endoscope apparatus comprising:
    an endoscope body that has an elongated insert portion having flexibility and capable of being inserted into a space which is a target of inspection;
    a remote controller having a flexibly bending operation portion which operates a flexibly bending portion provided at the insert portion to be flexibly bent;
    a manipulating device inserting channel which communicates between a distal opening end that opens at a distal end side of the insert portion of the endoscope body and a proximal opening end that opens at a proximal end of the insert portion of the endoscope body; and
    a linking portion which detachably links the remote controller and a peripheral portion at the proximal opening end of the manipulating device inserting channel without completely surrounding the endoscope body, wherein the linking portion disposes the proximal opening end of the manipulating device inserting channel at a position which does not interfere with an operating region of the flexibly bending operation portion in the remote controller in a state in which a link is established between the remote controller and the peripheral portion of the proximal opening end.

2. The endoscope apparatus according to claim 1, wherein the linking portion is disposed on a face of the remote controller that is different from a face on which the flexibly bending operation portion of the remote controller is disposed.

3. The endoscope apparatus according to claim 1, wherein the linking portion is disposed on a side face of the remote controller.

4. The endoscope apparatus according to claim 1, wherein the linking portion is a fixing member fixed to one of at least the remote controller and the manipulating device inserting channel.

5. The endoscope apparatus according to claim 1, wherein the linking portion is a fixing device capable of linking the remote controller and the peripheral portion of the proximal opening end at an arbitrary position of an axial direction of the insert portion.

6. The endoscope apparatus according to claim 1, wherein the manipulating device inserting channel is an incorporated channel incorporated in the insert portion.

7. The endoscope apparatus according to claim 1, wherein the manipulating device inserting channel is an external channel externally provided at the insert portion.

8. The endoscope apparatus according to claim 1, wherein the flexibly bending operation portion is a joystick which comprises an operating lever turnably supported at a proximal end portion via a turning fulcrum and generates a signal corresponding to a tilt angle of the operating lever.

9. An endoscope apparatus comprising:
    an insert portion which includes a flexibly bending portion having flexibility, the flexibly bending portion being provided at a distal end side, into a space which is a target of inspection;

a manipulating device inserting channel which loads therein a predetermined manipulating device advancing from a proximal end side of the insert portion to a distal end side of the insert portion;

a flexible bending operation portion to flexibly bend the flexibly bending portion of the insert portion remotely by a rod portion operation; and a connecting device which detachably mounts the flexible bending operation portion to the insert portion at the manipulating device inserting channel without completely surrounding the insert portion to make the flexible bending operation portion and the insert portion adjacent to each other, and links the flexible bending operation portion and the insert portion with each other such that an operating space of the rod portion operation and a loading space required for loading the predetermined manipulating device therein do not overlap each other.

10. The endoscope apparatus according to claim 9, wherein the connecting device is disposed on a face which is different from a face on which a rod portion of the flexible bending operation portion is disposed.

11. The endoscope apparatus according to claim 9, wherein the connecting device is disposed on a side face of the flexibly bending operation portion.

12. An endoscope apparatus comprising:

an elongated insert portion having flexibility, the elongated insert portion being inserted into a space which is a target of inspection;

an intermediate linking portion whose one end is linked with a proximal end side of the insert portion and whose other end is linked with a universal cable;

a controller comprising a flexibly bending operation portion to operate a flexibly bending portion provided at the insert portion to be flexibly bent;

a manipulating device inserting channel which communicates between a distal opening end that opens at a distal end side of the insert portion and a proximal opening end that opens at the intermediate linking portion; and a linking portion which detachably links the controller and the intermediate linking portion without completely surrounding the intermediate linking portion, wherein the linking portion disposes the proximal opening of the manipulating device inserting channel at a position which does not interfere with an operating region of the flexibly bending operation portion in the controller in a state in which a link is established between the controller and the intermediate linking portion.

13. The endoscope apparatus according to claim 12, wherein the linking portion is disposed on a face which is different from a face on which the flexibly bending operation portion of the controller is disposed.

14. The endoscope apparatus according to claim 12, wherein the linking portion is disposed on a side face of the controller.

15. An endoscope apparatus comprising:

an endoscope body including an elongated insert portion having flexibility and capable of being inserted into a space that is a target of inspection;

a remote controller including an operation portion operable to bend and drive the endoscope body;

an intermediate linking portion that communicates between a distal opening end of the insert portion and a proximal opening of the insert portion of the endoscope body, the intermediate linking portion having a manipulating device inserting channel that is open at both ends; and a connecting device that is attached to the remote controller at a position where it does not interfere with an operating region of the operation portion and into which the immediate linking portion is removably fit, the connecting device including a lock portion, into which the intermediate linking portion is removably fit, at a position where an insertion operating region of a manipulating device inserted through the proximal opening of the insert portion does not interfere with an operating region of the operation portion in the remote controller, when the intermediate linking portion is fitted into the connecting device attached to the remote controller without being completely surrounded by the connecting device.

16. The endoscope apparatus according to claim 15, wherein the lock portion of the connecting device has at least two U-shaped grooves, into which the intermediate linking portion is fit.

17. The endoscope apparatus according to claim 15, wherein the connecting device is disposed on a face which is different from a face on which the operation portion of the remote controller is disposed.

18. The endoscope apparatus according to claim 15, wherein the connecting device is disposed on a side face of the operation portion.

19. The endoscope apparatus according to claim 15, wherein the manipulating device inserting channel is an incorporated channel incorporated in the insert portion.

20. The endoscope apparatus according to claim 15, wherein the manipulating device inserting channel is an external channel externally provided at the insert portion.

21. The endoscope apparatus according to claim 15, wherein the operation portion is a joystick which is turnably supported about a fulcrum and generates a signal corresponding to a tilt angle of a peripheral portion.

22. The endoscope apparatus according to claim 15, wherein the intermediate linking portion links the insert portion with a universal cable.

23. The endoscope apparatus according to claim 15, further comprising a belt clamp configured to detachably hold the connecting device.

* * * * *